US012599696B2

(12) United States Patent
Dunkley et al.

(10) Patent No.: US 12,599,696 B2
(45) **Date of Patent: \*Apr. 14, 2026**

(54) HYDRATABLE AND FLOWABLE IMPLANTABLE COMPOSITIONS AND METHODS OF MAKING AND USING THEM

(71) Applicant: Warsaw Orthopedic, Inc., Warsaw, IN (US)

(72) Inventors: Ian Dunkley, Irvine, CA (US); Gretchen Selders, Memphis, TN (US)

(73) Assignee: Warsaw Orthopedic, Inc., Warsaw, IN (US)

( \* ) Notice: Subject to any disclaimer, the term of this patent is extended or adjusted under 35 U.S.C. 154(b) by 698 days.

This patent is subject to a terminal disclaimer.

(21) Appl. No.: 17/868,066

(22) Filed: Jul. 19, 2022

(65) Prior Publication Data

US 2022/0387663 A1     Dec. 8, 2022

Related U.S. Application Data

(63) Continuation-in-part of application No. 16/523,259, filed on Jul. 26, 2019, now Pat. No. 11,433,159.

(51) Int. Cl.
A61L 24/00     (2006.01)
A61L 24/10     (2006.01)

(52) U.S. Cl.
CPC ....... *A61L 24/0036* (2013.01); *A61L 24/0047* (2013.01); *A61L 24/102* (2013.01)

(58) Field of Classification Search
None
See application file for complete search history.

(56) References Cited

U.S. PATENT DOCUMENTS

| | | |
|---|---|---|
| 6,316,091 B1 | 11/2001 | Richart et al. |
| 6,340,648 B1 | 1/2002 | Imura et al. |
| 7,172,629 B2 | 2/2007 | McKay |
| 7,842,300 B2 | 11/2010 | Atkinson et al. |
| 8,048,857 B2 | 11/2011 | McKay et al. |
| 8,431,147 B2 | 4/2013 | Drapeau et al. |
| 8,486,080 B2 | 7/2013 | McKay |
| 8,653,029 B2 | 2/2014 | Vickers et al. |
| 8,926,552 B2 | 1/2015 | Walsh |
| 8,926,710 B2 | 1/2015 | McKay |
| 8,968,323 B2 | 3/2015 | McKay |
| 9,034,358 B2 | 5/2015 | Behnam et al. |
| 9,056,150 B2 | 6/2015 | Gross et al. |

| | | | |
|---|---|---|---|
| 2008/0031914 A1 | 2/2008 | Drapeau | C08L 89/06 424/423 |
| 2008/0147065 A1 | 6/2008 | McKay et al. | |
| 2011/0028393 A1 | 2/2011 | Vickers et al. | |
| 2012/0310366 A1 | 12/2012 | Li | A61K 31/505 623/23.57 |
| 2014/0341964 A1 | 11/2014 | McKay et al. | |
| 2015/0072017 A1 | 3/2015 | Kim et al. | |
| 2018/0353654 A1* | 12/2018 | Reves | A61L 27/3633 |

FOREIGN PATENT DOCUMENTS

| | | |
|---|---|---|
| CA | 2439813 A1 | 9/2002 |
| CN | 101396570 A | 4/2009 |
| CN | 108601864 A | 9/2018 |
| JP | H06296678 A | 10/1994 |
| WO | 2008016891 A1 | 2/2008 |

OTHER PUBLICATIONS

European Office Action. European Patent Office. European Appl. No. 20846779.5-1109. dtd Apr. 26, 2024. 6 pgs.
China National Intellectual Property Administration, Application No. 202080049742.7, 1 Applicant: Warsaw Orthopedic, Inc., Decision on Rejection, Date of Dispatch: Dec. 14, 2022.
European Patent Office. Supplementary European Search Report. Application No. 20848678.7. Dispatch Date: Apr. 21, 2023.
Daculsi, G., et al., Key Engineering Materials 529-530: 19-23 (Nov. 29, 2012). (Year: 2012).
China National Intellectual Property Administration, Notice on the Second Office Action, Application/Patent No. 202080049697.5, Date of Dispatch—Feb. 5, 2023.
China National Intellectual Property Administration, Decision on Rejection, Application No. 202080049697.5, Date of Dispatch Apr. 29, 2023.
European Office Action, European Appl No. 20 848 678.7-1109. dtd Jul. 9, 2024. 3 pgs.
European Office Action. European Patent Office. European Application No. 20 846 779.5-1109. dtd Oct. 24, 2025. 7 pages.

* cited by examiner

*Primary Examiner* — David J Blanchard
*Assistant Examiner* — Daniel F Coughlin
(74) *Attorney, Agent, or Firm* — Sorell, Lenna & Schmidt, LLP

(57)     ABSTRACT

Implantable bone compositions are provided. The implantable compositions comprise hydratable bone putties. The hydratable bone putties comprise porous ceramic granules having an average diameter from about 50 µm to 800 µm and the composition has a texture value above about 1000. The porous ceramic granules comprise hydroxyapatite and beta-tricalcium phosphate. The implantable bone compositions further include collagen carriers. In some embodiments, the hydratable bone putty can be hydrated to form a non-settable flowable cohesive cement or gel. Methods of making and using the implantable compositions are also provided.

15 Claims, 17 Drawing Sheets

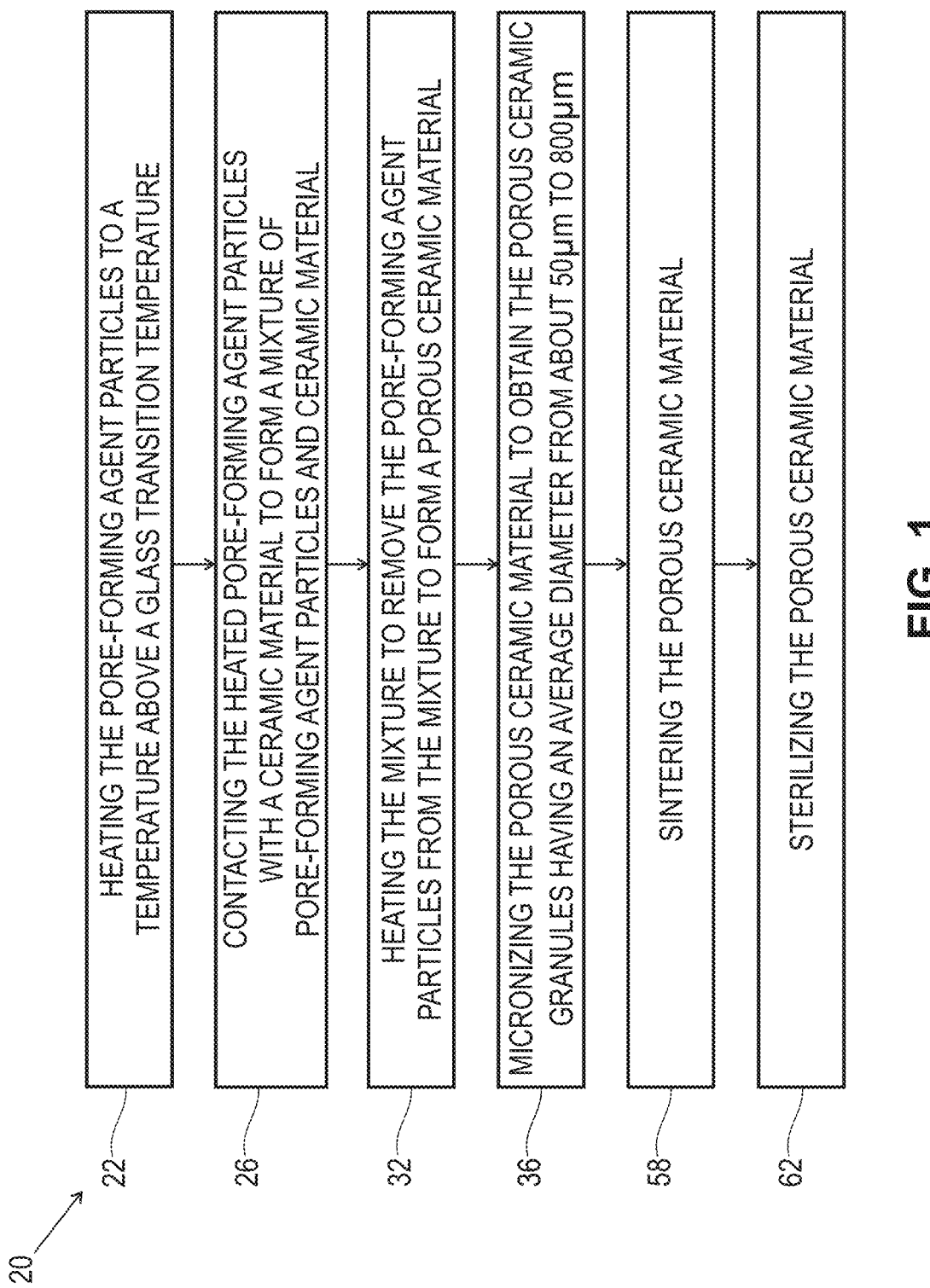

HEATING THE PORE-FORMING AGENT PARTICLES TO A TEMPERATURE ABOVE A GLASS TRANSITION TEMPERATURE

CONTACTING THE HEATED PORE-FORMING AGENT PARTICLES WITH A CERAMIC MATERIAL TO FORM A MIXTURE OF PORE-FORMING AGENT PARTICLES AND CERAMIC MATERIAL

HEATING THE MIXTURE TO REMOVE THE PORE-FORMING AGENT PARTICLES FROM THE MIXTURE TO FORM A POROUS CERAMIC MATERIAL

MICRONIZING THE POROUS CERAMIC MATERIAL TO OBTAIN THE POROUS CERAMIC GRANULES HAVING AN AVERAGE DIAMETER FROM ABOUT 50μm TO 800μm

SINTERING THE POROUS CERAMIC MATERIAL

STERILIZING THE POROUS CERAMIC MATERIAL

FIG. 1

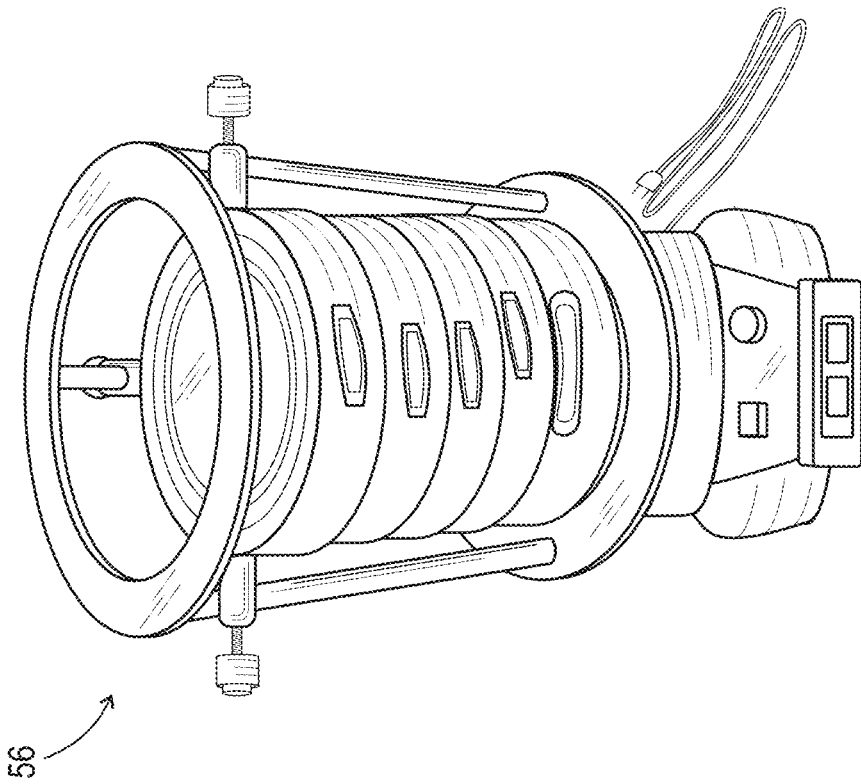
56
FIG. 8
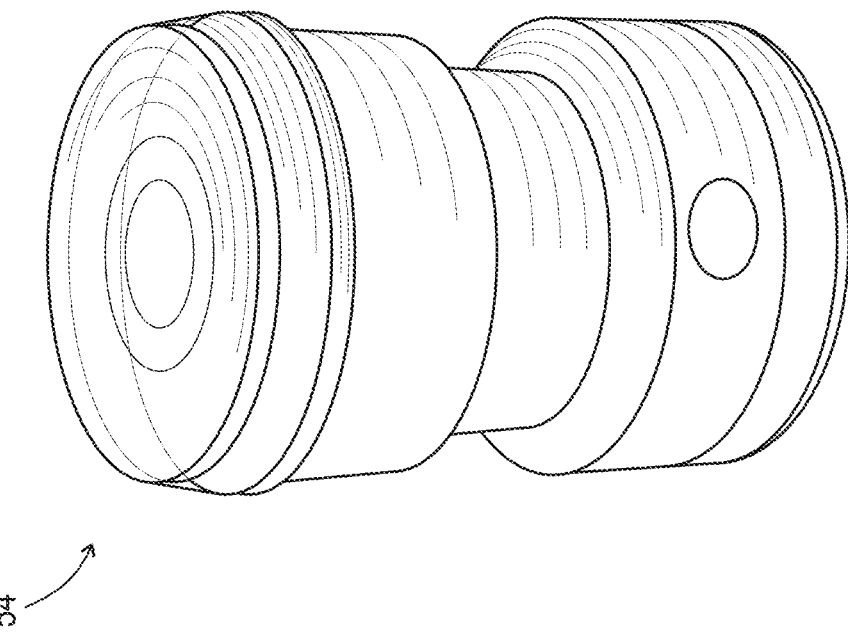
54

DEHYDRATED COMPOSITION

ADDING A FLUID TO THE DEHYDRATED COMPOSITION

FORMING A HYDRATED PUTTY

ADDING A FLUID TO THE HYDRATED PUTTY

FORMING A NON-SETTABLE AND FLOWABLE CEMENT OR GEL

HYDRATABLE AND FLOWABLE IMPLANTABLE COMPOSITIONS AND METHODS OF MAKING AND USING THEM

BACKGROUND

Bone defects or bone voids may be caused by a number of different factors, including but not limited to trauma, pathological disease or surgical intervention. Because bone provides both stability and protection to an organism, these defects or voids can be problematic. In order to address these defects or voids, compositions that contain both natural and synthetic materials have been developed. These compositions may, depending upon the materials contained within them, be used to repair tissues and to impart desirable biological and/or mechanical properties.

At times, to treat bone defects, osteoimplants can be used, such as for example, bone void fillers. Bone void fillers can be in the form of bone cements or bone putties. Bone cements are typically used to assist in the attachment of artificial implants to living bone or fill bone voids in order to repair the damaged bone. Bone putties are generally used to fill bone voids and can also be used to stimulate regeneration of bone.

Bone cements and bone putties can be desirable to use due to their handling characteristics such as flowability and moldability, which facilitates placement into irregularly shaped bone repair sites (e.g., bone defects or bone voids). For example, often, when the bone repair site is a bone void, a surgeon may administer a bone cement to the bone void through the use of a cannula or the surgeon may administer a bone putty to the bone void by molding and shaping the putty into the bone void by hand.

Typically, bone cements and bone putties are made from particulated bone dispersed in a biodegradable polymer, such as alginate or polyethylene glycol (PEG). While these polymers provide good handling characteristics for administering the cement or putty to a bone repair site, they may not perform optimally for bone growth once implanted into the bone void.

Further, bone cements and bone putties can include scaffolding materials, such as, biocompatible synthetic ceramics. However, while these materials can be beneficial for bone growth, they may be difficult to incorporate in substantial amounts into a composition that has a putty-like consistency since these ceramics are generally larger in size, non-uniform, hard and brittle. Moreover, the addition of large hard pieces of ceramic tends to disrupt the bone putty mass, producing a composition that is unstable and lacks the desired cohesiveness for handling prior to implantation and for a stable putty after implantation at the bone repair site.

Many available bone putties or pastes cannot be readily converted into non-settable flowable cements or gels nor can non-settable flowable cements or gels be readily converted into putties or pastes. Typically, when additional fluid is added to an already formed bone putty or paste, a non-settable flowable and injectable bone cement or gel cannot be formed as the over hydrated bone putty or paste lacks cohesion, becomes unstable, and disintegrates.

Therefore, there is a need for a composition that can be converted from a putty or paste into a non-settable flowable cement or gel, and also once the composition is in the non-settable flowable cement or gel form, the composition can be readily converted into a putty or paste. There is also a need to provide a composition that has flexible handling characteristics that allow the composition to be made into a putty, paste, non-settable flowable cement or a non-settable flowable gel.

SUMMARY

Compositions are provided that can be converted from a putty or paste into a non-settable flowable cement or gel, and also once the composition is in the non-settable flowable cement or gel form, the composition can be readily converted into a putty or paste. In some embodiments, the composition can be hydrated with a fluid to form a stable bone putty, where, if desired, the bone putty can be further hydrated with a fluid to form a stable and non-settable flowable cement or gel. The bone putty and the non-settable flowable cement or gel provided can be moldable and flow through a cannula for administration to a surgical site. In some embodiments, the composition can be readily mixed with a patient's own bone material to provide the desired consistency in a putty, paste, non-settable cement or non-settable flowable gel.

In some embodiments, an implantable composition is provided. The implantable composition comprises a hydratable putty. The hydratable putty comprises porous ceramic granules having an average diameter from about 50 μm to 800 μm. The porous ceramic granules comprise hydroxyapatite and beta-tricalcium phosphate. The composition further includes a collagen carrier.

In some embodiments, a hydratable putty is provided. The hydratable putty comprises porous ceramic granules having an average diameter from about 50 μm to 800 μm and comprising hydroxyapatite and beta-tricalcium phosphate. The hydratable putty includes a collagen carrier comprising type I collagen.

In some embodiments, a method of making an implantable composition is provided. The method comprises hydrating a hydratable putty with a fluid, the hydratable putty comprising porous ceramic granules in a collagen carrier, the porous ceramic granules comprising hydroxyapatite in an amount of about 8 to about 22 wt. % and beta-tricalcium phosphate in an amount of about 78 to about 92 wt. %, the porous ceramic granules having an average diameter from about 50 μm to 800 μm.

In some embodiments, an implantable composition is provided. The composition comprises porous ceramic granules. The porous ceramic granules comprise hydroxyapatite in an amount of about 8 to about 22 wt. % and beta-tricalcium phosphate in an amount of about 78 to about 92 wt. % based on a total weight of a ceramic granule. The composition includes a collagen carrier, and the porous ceramic granules have an average diameter from about 50 μm to 800 μm.

In some embodiments, a bone void filler is provided. The bone void filler comprises porous ceramic granules comprising hydroxyapatite in an amount of about 8 to about 22 wt. % and beta-tricalcium phosphate in an amount of about 78 to about 92 wt. %. The porous ceramic granules have an average diameter from about 50 μm to 800 μm. The bone void filler includes a collagen carrier comprising bovine type I collagen.

In some embodiments, a method of making a moldable and flowable bone void filler is provided. The method comprises adding porous ceramic granules to a collagen carrier, the porous ceramic granules comprising hydroxyapatite in an amount of about 8 to about 22 wt. % and beta-tricalcium phosphate in an amount of about 78 to about 92 wt. %.

In some embodiments, a method of making porous ceramic granules is provided. The method comprises heating pore-forming agent particles to a temperature above a glass transition temperature for the pore-forming agent particles; contacting the heated pore-forming agent particles with a ceramic material to form a mixture of pore-forming agent particles and ceramic material; heating the mixture to remove the pore-forming agent particles from the mixture to form a porous ceramic material; and micronizing the porous ceramic material to obtain the porous ceramic granules, wherein the porous ceramic granules have an average diameter from about 50 μm to 800 μm.

In some embodiments, porous ceramic granules are provided. The porous ceramic granules are made by the process of heating pore-forming agent particles to a temperature above a glass transition temperature for the pore-forming agent particles; contacting the heated pore-forming agent particles with a ceramic material to form a mixture of pore-forming agent particles and ceramic material; heating the mixture to remove the pore-forming agent particles from the mixture to form porous ceramic material; and micronizing the porous ceramic material to obtain the porous ceramic granules, wherein the porous ceramic granules have an average diameter from about 50 μm to 800 μm.

In some embodiments, a porous ceramic granule is provided. The porous ceramic granule comprises hydroxyapatite in an amount of about 8 to about 22 wt. % and beta-tricalcium phosphate in an amount of about 78 to about 92 wt. %. The porous ceramic granule has a microporosity and a diameter of each of the micropores is less than about 10 μm, a BET surface area from about 0.2 to about 10 m²/g, and an average diameter from about 50 μm to 800 μm.

In some embodiments, there is an implantable composition comprising porous ceramic granules, the porous ceramic granules having an average diameter from about 50 μm to 800 μm and comprising hydroxyapatite and beta-tricalcium phosphate; and a collagen carrier, the composition having a texture value greater than 1000.

In some embodiments, there is a composition comprising porous ceramic granules, the porous ceramic granules having an average diameter from about 50 μm to 800 μm and comprising hydroxyapatite and beta-tricalcium phosphate; and a collagen carrier comprising bovine type I collagen, wherein the porous ceramic granules have a microporosity, and the diameter of each of the micropores is from about 0.01 to about 10 microns, and each of the porous ceramic granules has a Brunauer-Emmett-Teller (BET) surface area from about 0.2 to about 10 m²/g, wherein the composition comprises from about 77 to about 93 wt. % porous ceramic granules and from about 7 to about 23 wt. % of the collagen carrier, wherein the composition has a texture value greater than 1000.

In some embodiments, there is a method of making an implantable composition, the method comprising hydrating the composition with a fluid to form a hydrated composition, the hydrated composition comprising porous ceramic granules in a collagen carrier, the porous ceramic granules comprising hydroxyapatite in an amount of about 8 to about 22 wt. % and beta-tricalcium phosphate in an amount of about 78 to about 92 wt. %, the porous ceramic granules having an average diameter from about 50 μm to 800 μm, wherein the composition has a texture value greater than 1000.

While multiple embodiments are disclosed, still other embodiments of the present application will become apparent to those skilled in the art from the following detailed description, which is to be read in connection with the accompanying drawings. As will be apparent, the present disclosure is capable of modifications in various obvious aspects, all without departing from the spirit and scope of the present disclosure. Accordingly, the detailed description is to be regarded as illustrative in nature and not restrictive.

BRIEF DESCRIPTION OF THE DRAWINGS

In part, other aspects, features, benefits and advantages of the embodiments will be apparent regarding the following description, appended claims and accompanying drawings.

FIG. 1 is a flow chart of the method of making the porous ceramic granules. The method comprises heating pore-forming agent particles to a temperature above a glass transition temperature for the pore-forming agent particles; contacting the heated pore-forming agent particles with a ceramic material to form a mixture of pore-forming agent particles and ceramic material; heating the mixture to remove the pore-forming agent particles from the mixture to form a porous ceramic material; and micronizing the porous ceramic material to obtain the porous ceramic granules, wherein the porous ceramic granules have an average diameter from about 50 μm to 800 μm.

FIG. 8 is a perspective view of an automated crusher and an automated sieve that in some embodiments, are used to micronize the porous ceramic material.

Figure 2:
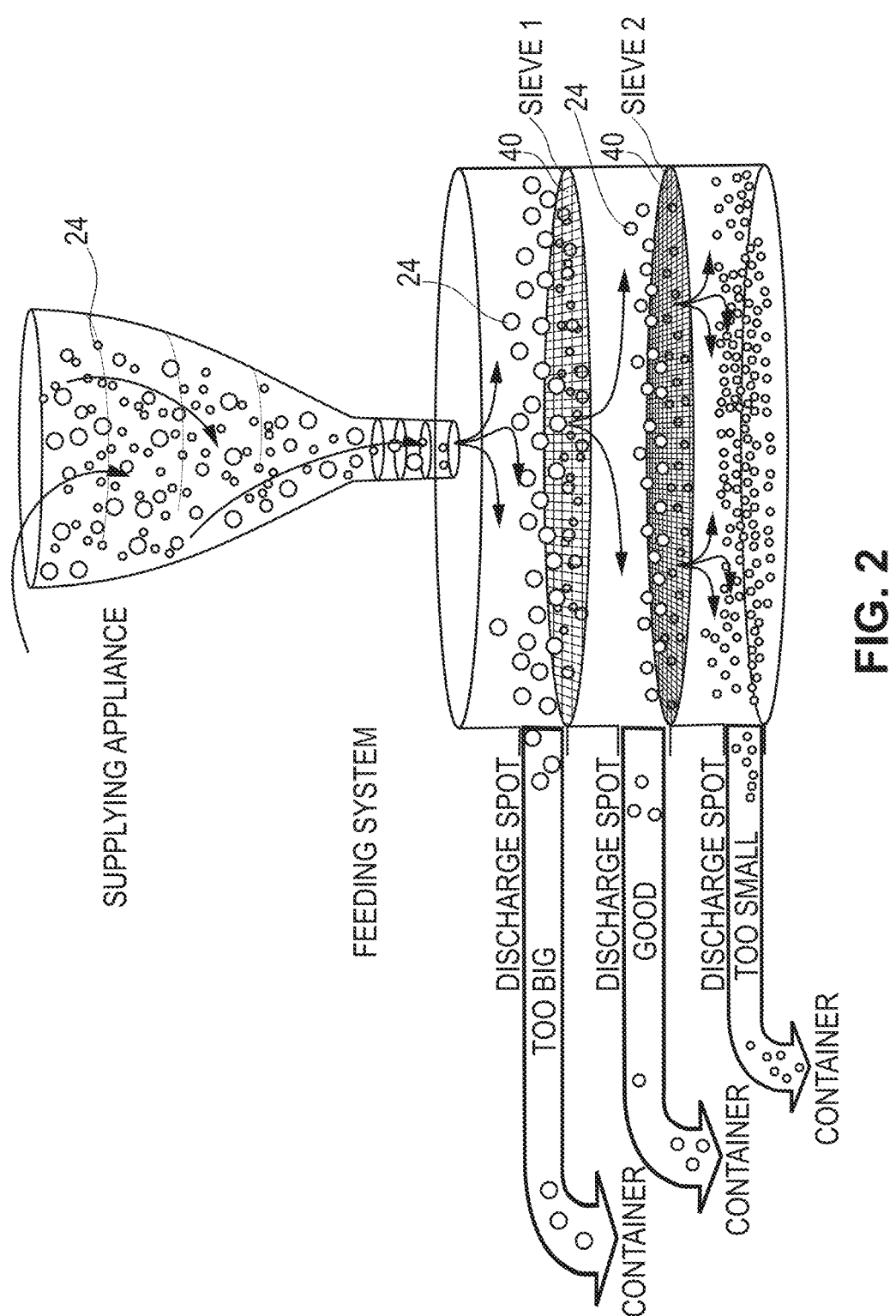
FIG. 2 is a front view of pore-forming agent particles such as polymethyl methacrylate (PMMA) that are fed through a plurality of sieves to calibrate the pore-forming particles to a selected size for use.

It is to be understood that the figures are not drawn to scale. Further, the relation between objects in a figure may not be to scale and may in fact have a reverse relationship as to size. The figures are intended to bring understanding and clarity to the structure of each object shown, and thus, some features may be exaggerated in order to illustrate a specific feature of a structure.

DETAILED DESCRIPTION

Definitions

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Similarly, when values are expressed as approximations, by use of the antecedent "about," it will be understood that the particular value forms another embodiment that is +/−10% of the recited value. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value.

Notwithstanding that the numerical ranges and parameters setting forth the broad scope of this application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Biocompatible, as used herein, is intended to describe materials that, upon administration in vivo, do not induce undesirable long-term effects.

Bone, as used herein, refers to bone that is cortical, cancellous or cortico-cancellous of autogenous, allogenic, xenogenic, or transgenic origin.

The term "autograft" refers to graft material harvested from the same individual patient who is also recipient of the graft, obtained surgically from non-essential donation sites in the patient.

Bone graft, as used herein, refers to any implant prepared in accordance with the embodiments described herein and therefore may include expressions such as a bone void filler.

The term "osteoinductive," as used herein, refers to the quality of being able to recruit cells from the host that have the potential to stimulate new bone formation. Any material that can induce the formation of ectopic bone in the soft tissue of an animal is considered osteoinductive.

The term "osteoinduction" refers to the ability to stimulate the proliferation and differentiation of pluripotent mesenchymal stem cells (MSCs). In endochondral bone formation, stem cells differentiate into chondroblasts and chondrocytes, laying down a cartilaginous ECM, which subsequently calcifies and is remodeled into lamellar bone. In intramembranous bone formation, the stem cells differentiate directly into osteoblasts, which form bone through direct mechanisms. Osteoinduction can be stimulated by osteogenic growth factors, although some ECM proteins can also drive progenitor cells toward the osteogenic phenotype.

The term "osteogenic" refers to the ability of a graft material to produce bone independently. To have direct osteogenic activity, the graft must contain cellular components that directly induce bone formation. For example, an allograft seeded with activated MSCs would have the potential to induce bone formation directly, without recruitment and activation of host MSC populations. Because many osteoconductive allografts also have the ability to bind and deliver bioactive molecules, their osteoinductive potential will be greatly enhanced.

The term "patient" refers to a biological system to which a treatment can be administered. A biological system can include, for example, an individual cell, a set of cells (e.g., a cell culture), an organ, or a tissue. Additionally, the term "patient" can refer to animals, including, without limitation, humans.

The term "implantable" as utilized herein refers to a biocompatible device (e.g., the composition) retaining potential for successful placement within a mammal. The expression "implantable composition" and expressions of the like import as utilized herein refers to an object implantable through surgery, injection, or other suitable means whose primary function is achieved either through its physical presence or mechanical properties. An example of the implantable device is the composition.

The term "thermoform" or "thermoforming" refers to the process where a material such as plastic is heated to a pliable forming or glass transition temperature to form a specific shape in a mold.

The "debind," or "debinding" refers to a process to remove a primary binding material from a mold. The mold can be created through a thermoforming process, as described above. Typically, there are multiple steps to the debinding process, and the part goes through more than one cycle to ensure as much of the binding material is removed as possible before sintering. After the debinding process, the part can be semi-porous, which can allow a secondary material to easily escape during a sintering cycle.

The term. "amorphous" is defined a structure has no organization (not a crystalline structure), and the atomic structure resembles that of a liquid. Commonly, amorphous materials are amorphous solids unless otherwise clarified. Amorphous materials are characterized by atomic or molecular structures that are relatively complex and become ordered only with some difficultly. These materials are commonly prepared by rapidly cooling molten material. The cooling reduces the mobility of the material's molecules before they can pack into a more thermodynamic state.

The terra "crystalline" is defined as a material that consists primarily of an organized crystal structure. A "crystal" is a solid composed of atoms, ions, or molecules arranged in a pattern that is repetitive in three-dimensions. Each crystal structure within a specific crystal system is defined by a unit cell. A unit cell is the smallest repeatable subsection of the crystal.

The term "moldable" includes that the composition can be shaped by hand or machine or injected into the target tissue site (e.g., hone defect, fracture, or void) into a wide variety of configurations to fit within the bone defect.

The terra "cohesive" as used herein means that the composition tends to remain a singular, connected mass upon the addition of fluid, autograft bone or during manipulation, including the exhibition of the ability to be molded or shaped without breaking upon manipulating, or disintegrating or becoming unstable.

The term "flowable" includes that the composition can be administered in an injectable state via a syringe and/or cannula. The composition is flowable when its consistency is fluid-like and has a viscosity that is lower than that of the viscosity of the composition when in a putty or paste form. Plowable compositions include liquid (e.g., solution, suspension, or the like) or semi-solid compositions (e.g., gels, cements) that are easy to manipulate and may be brushed, sprayed, dripped, injected, shaped and/or molded at or near the target tissue site. "Plowable" includes compositions with a low viscosity or water-like consistency to those with a high viscosity, such as a paste-like material. In various embodiments, the flowability of the composition allows it to conform to irregularities, crevices, cracks, and/or voids in the bone defect site (e.g., bone void). For example, in various embodiments, the composition may be used to fill one or more voids in an osteolytic lesion.

The term "injectable" refers to a mode of administering the composition. The composition can be administered in a variety of ways such as, for example, a syringe and/or cannula. For example, the composition can be administered parenterally, such as for example, anterior lumbar interbody administration for fusion, or posterior lumbar interbody administration for fusion or transforaminal lumbar interbody administration for fusion, other intraspinal injection or other local administration.

The term "hydrate," "hydration," "hydratable," "hydrating" or "hydrated" refers to adding an amount of fluid to a composition to increase the amount of moisture content in the composition to form a putty, paste and/or a non-settable flowable cohesive cement or gel.

The term "dehydrated" or "dehydration" refers to a composition that contains a small amount of residual moisture or no moisture content and can be in the form of a dry composition. The dehydrated composition can have a moisture content from about 0 to about 10% based on the total weight of the composition. In some embodiments, when a composition is dehydrated, fluid can be added to the composition to hydrate the composition. A dehydrated composition includes a lyophilized or freeze-dried composition.

The term "bone marrow aspirate" or "BMA" refers to the withdrawal of bone marrow fluid through a syringe and needle to harvest the bone marrow fluid from the patient. Bone marrow aspirate comprises fluid that contains a heterogeneous mix of stem and progenitor cells, platelets and white blood cells. The bone marrow aspirate can be harvested from various sources in the body, including, but not limited to the iliac crest.

The term. "soluble collagen" refers to the solubility of individual tropocollagen molecules in acidic aqueous environments. Tropocollagen may be considered the monomeric unit of collagen fibers and its triple helix structure is well recognized.

"Insoluble collagen" as used herein refers to collagen that cannot be dissolved in an aqueous alkaline or in any inorganic salt solution without chemical modification, and includes for example hides, splits and other mammalian or reptilian coverings. For example, "natural insoluble collagen" can be derived from the corium, which is the intermediate layer of an animal hide (e.g. bovine, porcine, fish, etc.) that is situated between the grain and the flesh sides.

Method of Making Porous Ceramic Granules

Methods of making a porous ceramic granule are provided that can be tailored to have a specific size, porosity and microporosity that provide better handling characteristics when administered to a bone defect in a bone void filler.

As shown in FIGS. 1-10, a method of making porous ceramic granules is provided. The method allows the production of ceramic granules of a selected size, porosity, microporosity that have a specific surface area that is beneficial for bone growth when administered to a bone defect as a bone graft such as, for example, a bone void filler.

As shown in the flow chart of FIG. 1, the method 20 comprises heating 22 pore-forming agent particles 24 to a temperature above a glass transition temperature for the pore-forming agent particles; contacting 26 the heated pore-forming agent particles with a ceramic material 28 to form a mixture 30 of pore-forming agent particles and ceramic material; heating 32 the mixture to remove the pore-forming agent particles from the mixture to form a porous ceramic material 34; and micronizing 36 the porous ceramic material to obtain the porous ceramic granules 38, wherein the porous ceramic granules have an average diameter from about 50 µm to 800 µm.

The pore-forming agent particles can be polymeric, such as, for example, a thermoplastic polymer. Thermoplastic polymers can include, but are not limited to, polymethyl methacrylate (PMMA), polymethacrylate (PMA), polystyrene, polyethylene or a combination thereof. In some embodiments, the thermoplastic polymer selected is PMMA.

The pore-forming agent particles can be a specific size and each particle can have the same or different dimensions. It is contemplated that the particle size of the pore-forming agent particles can determine the macropore size as well as the microporosity of the final porous ceramic granules formed from the method. As shown in FIG. 2, a plurality of stacked sieves 40 having different pore or mesh sizes can be used to separate the pore-forming agent particles by size to obtain the selected size for use in the method.

For example, pore-forming agent particles that are selected for use would be particles having a size range of from about 40 to about 700 µm. The particles, in some embodiments, can be in a range from about 500 to about 670 µm, or from about 550 to about 600 µm. The pore-forming agent particles can be from about 40, 50, 60, 70, 80, 90, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695 to about 700 µm.

The pore-forming agent particles can be an at least partially amorphous structure or a completely amorphous structure so as to avoid too great a volume increase during heat treatment. In some embodiments, the pore-forming agent particles are in the form of beads. Other shaped particles can be used including square, oval, irregularly shaped or a combination thereof.

The pore-forming agent particles are configured to degrade at a low temperature or a glass transition temperature such that the particles can coalesce to form a monobloc or interconnected porous structure for the ceramic material to interact with. For example, in the case of PMMA, the glass transition temperature is about 110° C. The pore-forming agent particles can degrade at a low temperature with only a small amount of residual impurities and of non-corrosive decomposition products. A thermoforming process can be used to heat the pore-forming agent particles.

As described above, the pore-forming agent particles are first heated to a temperature by a thermoforming process above a glass transition temperature for the selected pore-forming agent particles. For example, the temperature can be from 150 about to about 250° C. In some embodiments, the temperature can be from about 150° C. to about 180° C. The temperature can be from about 150, 155, 160, 165, 170, 175, 180, 185, 190, 195, 200, 205, 210, 215, 220, 225, 230, 235, 240, 245 to about 250° C. The particles can be heated for a period of time from about 14 to about 18 hours. The particles can be heated for a period time from about 14, 15, 16, 17 to about 18 hours.

Figures 3A, 3B:
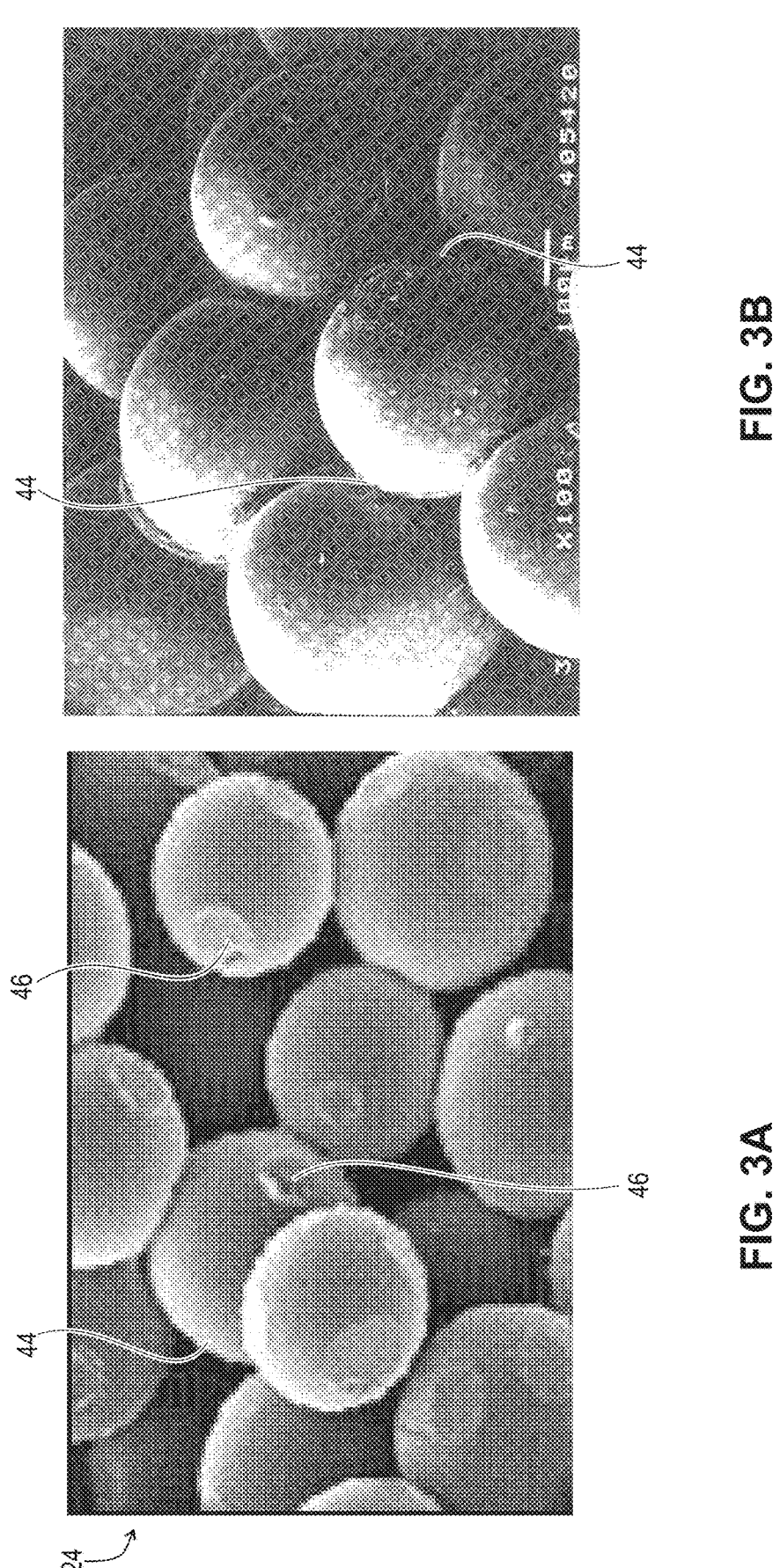
FIG. 3A is a SEM micrograph showing portions of the pore-forming agent particles that overlap diameters when the particles coalesce and interconnect.
FIG. 3B is an SEM micrograph of a portion of an interconnected porous structure that is formed during heating of the pore-forming agent particles in a thermoforming process.

When the pore-forming agent particles are heated above their glass transition temperature, each of the particles contact one another and partially interlock to fuse the particles together. Once the heating step is completed, a monobloc or interconnected porous structure 42 is in a fixed state and contains pores or spaces 44 between the pore-forming agent particles, as shown in FIG. 3B. The pore-forming agent particles will contain overlapping diameters which can be visualized by a circle 46 on the exterior surface of each pore-forming agent particle, as shown in FIG. 3A. The circle indicates that an interconnection between beads has occurred and the circle is an interconnection rupture.

Prior to heating the pore-forming agent particles, the particles can be placed into a container that can withstand thermal degradation temperatures. The container can also be variously sized and shaped. Further, the container can be made from metal, plastic and/or aluminum. After the heating, the pore-forming agent particles now formed into the monobloc or interconnected porous structure can be placed into a new container or mold. The mold can be a porous mold.

Figure 6:
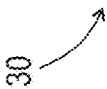
FIG. 6 illustrates a mixture of pore-forming agent particles and the ceramic material.

The next step is contacting the heated pore-forming agent particles with a ceramic material to form a mixture of pore-forming agent particles and ceramic material. In this step, the mixture of ceramic material fills in the pores or spaces created in between the pore-forming agent particles, as shown in FIG. 6. The mixture of ceramic material can be dispersed in a suspension or slurry 48. After contacting/adding the ceramic mixture to the pore-forming agent particles, the mixture can be air dried for a period of time such as, for about 3 hours, and can be further dried in a dryer for a period of time.

Figure 4:
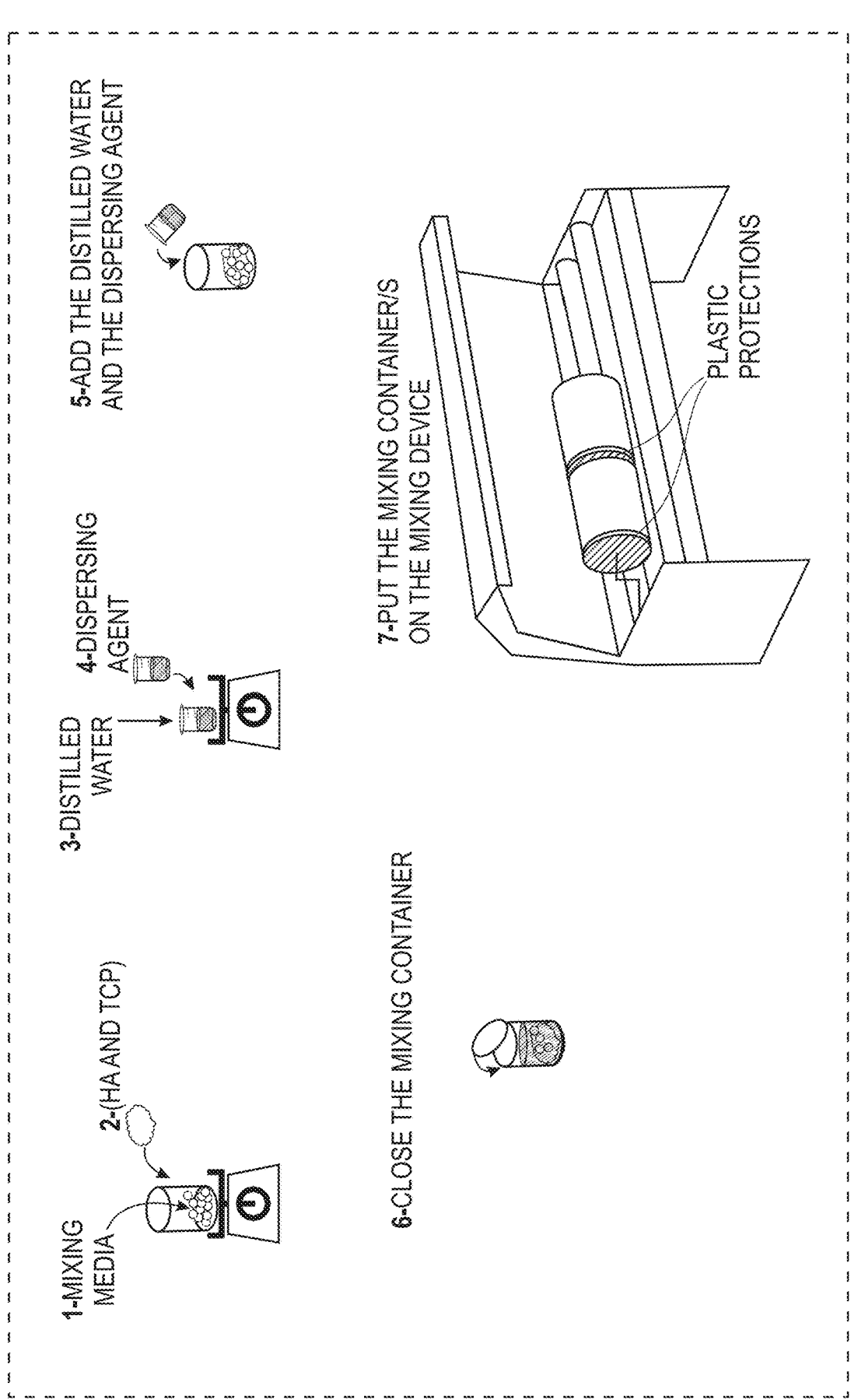
FIG. 4 illustrates the steps in making a ceramic material slurry that contacts the heated pore-forming agent particles to form a mixture of pore-forming agent particles and ceramic material. The ceramic material can be added to a mixing media to form a suspension or slurry.
Figure 5:
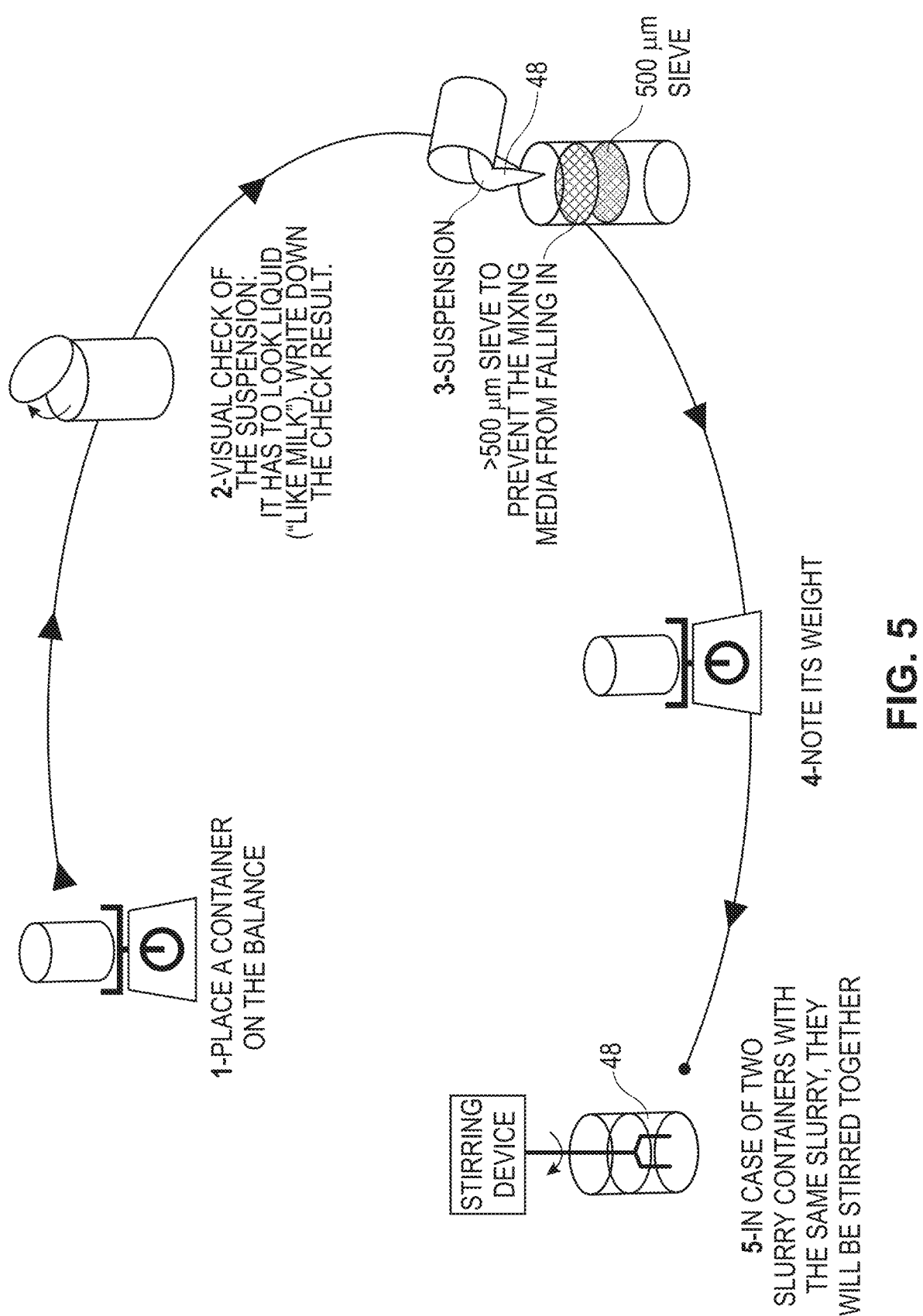
FIG. 5 illustrates the steps in making the ceramic slurry of FIG. 4 stirred before it contacts the heated pore-forming agent particles.

Before the ceramic material contacts with the heated pore-forming agent particles, the suspension or slurry of ceramic material is prepared. As shown in FIG. 4, the slurry or suspension can be made by adding the ceramic material to an amount of mixing media that is disposed in a container forming a mixture. An amount of distilled water and dispersing agent is then added to the mixture, and the container is closed. The container is then placed on a mixing device. As shown in FIG. 5, the container can then be placed on a balance to weigh the container with the mixture and can be visually inspected to see if the mixture has a "milk like" appearance. The mixture is then filtered through a sieve to remove the mixing media from the mixture. The resulting slurry or suspension is then placed into a second container. The weight of the container and slurry or suspension can be taken, and finally the container can be stirred with a stirring device (FIG. 5).

In some embodiments, the mixing media used to create the slurry or suspension can include materials such as, for example, sodium acetate buffer, sodium citrate buffer, sodium phosphate buffer, a Tris buffer (e.g., Tris-HCL), phosphate buffered saline (PBS), sodium phosphate, potassium phosphate, sodium chloride, potassium chloride, glycerol, calcium chloride or a combination thereof. In various embodiments, the buffer concentration can be from about 1 mM to 100 mM. In some embodiments, the mixing media can further include sucrose, glycine, L-glutamic acid, sodium chloride, and/or polysorbate 80. Exemplary organic solvents or non-aqueous solvents include DMSO, acetic acid, acetone, DME, DMF, MTBE, acetonitrile, butanol, butanone, t-butyl alcohol, ethanol, polyethylene glycol, methanol, chlorobenzene, chloroform, toluene, propanol, pentane, heptane, ethanol, diethyl ether, or the like.

In some embodiments, the mixing media can include a binding agent to help the slurry or suspension retain its shape when contacting the heated pore-forming agent particles. Examples of suitable binding agents include, but are not limited to glycerol, polyglycerol, polyhydroxy compound, for example, such classes of compounds as the acyclic polyhydric alcohols, non-reducing sugars, sugar alcohols, sugar acids, monosaccarides, disaccharides, water-soluble or water dispersible oligosaccharides, polysaccarides and known derivatives of the foregoing. Specific polyhydroxy compounds include, 1,2-propanediol, glycerol, 1,4-butylene glycol trimethylolethane, trimethylolpropane, erythritol, pentaerythritol, ethylene glycols, diethylene glycol, triethylene glycol, tetraethylene glycol, propylene glycol, dipropylene glycol; polyoxyethylene-polyoxypropylene copolymer, for example, of the type known and commercially available under the trade names Pluronic and Emkalyx; polyoxyethylene-polyoxypropylene block copolymer, for example, of the type known and commercially available under the trade name Poloxamer; alkylphenolhydroxypolyoxyethylene, for example, of the type known and commercially available under the trade name Triton, polyoxyalkylene glycols such as the polyethylene glycols, xylitol, sorbitol, mannitol, dulcitol, arabinose, xylose, ribose, adonitol, arabitol, inositol, fructose, galactose, glucose, mannose, sorbose, sucrose, maltose, lactose, maltitol, lactitol, stachyose, maltopentaose, cyclomaltohexaose, carrageenan, agar, dextran, alginic acid, guar gum, gum tragacanth, locust bean gum, gum arabic, xanthan gum, amylose, mixtures of any of the foregoing.

The ceramic material can comprise synthetic ceramic or ceramics including hydroxyapatite and beta-tricalcium phosphate. The ceramic material can be in a powder form. The ceramic material comprises a calcium to phosphate ratio of between 1.0 to about 2.0. In some embodiments, the calcium to phosphate ratio is between 1.0, 1.1, 1.2, 1.3, 1.4, 1.5, 1.6, 1.7, 1.8, 1.9 to about 2.0.

The ceramic material is a biphasic calcium phosphate comprising hydroxyapatite in an amount of about 8 to about 22 wt. % and beta-tricalcium phosphate in an amount of about 78 to about 92 wt. %. In some embodiments, the hydroxyapatite is in an amount of about 8, 9, 10, 11, 12, 13, 14, 15, 16, 17, 18, 19, 20, 21 to about 22 wt. % and the beta-tricalcium phosphate in an amount of about 78, 79, 80, 81, 82, 83, 84, 85, 86, 87, 88, 89, 90, 91 to about 92 wt. %.

The next step in the method is heating the mixture to remove the pore-forming agent particles from the mixture to form a porous ceramic material. This step can be considered a debinding or demolding step. In this step, heat is applied to the mixture to burn out the pore-forming agent particles, creating voids in the place of the pore-forming agent particles and leaving the porous ceramic material intact.

The mixture is heated at a temperature from about 200° C. to about 300° C. for a period of time and the heating can be done in an oven. The temperature can be from about 200, 205, 210, 215, 220, 225, 230, 235, 240, 245, 250, 255, 260, 265, 270, 275, 280, 285, 290, 295 to about 300° C. The heat treatment can be administered for a period of time from about 1 hour to about 20 hours. In some embodiments, the period of time is from about 1, 2, 3, 4, 5, 6, 7, 8, 9, 10, 11, 12, 13, 14, 15, 16, 17, 18, 19 to about 20 hours.

The next step in the method is micronizing the porous ceramic material to obtain the porous ceramic granules. The ceramic material can be granules that can be micronized and/or passed through a sieve to obtain the desired granule size. Micronization includes reducing the average diameter of porous ceramic granules. Typically, micronization includes using mechanical means to reduce the particle size of the porous ceramic granules, such as for example, by granulation, crushing, bashing, milling and/or grinding.

In some embodiments, a mill can be used to micronize the ceramic material, where the mill has a cylindrical drum that usually contains spheres. As the drum rotates the spheres inside collide with the ceramic material, thus crushing them towards smaller diameters. In some embodiments, with grinding, the ceramic granules can be formed when the grinding units of a device rub against each other while the granules are trapped in between them.

In some embodiments, methods like crushing and/or cutting may also be used for reducing particle size of the ceramic material. Crushing can employ, for example, hammer-like tools to break the porous ceramic into smaller particles by means of impact. In some embodiments, cutting can use sharp blades to cut the rough solid pieces into smaller ones. These micronization techniques can reduce the particle size of the ceramic to the micrometer size and these particles can be passed through one or more sieves by hand or machine to obtain the desired particle size of the porous ceramic granules. The resulting porous ceramic granules will have an average diameter from about 50 μm to 800 μm.

Figure 7:
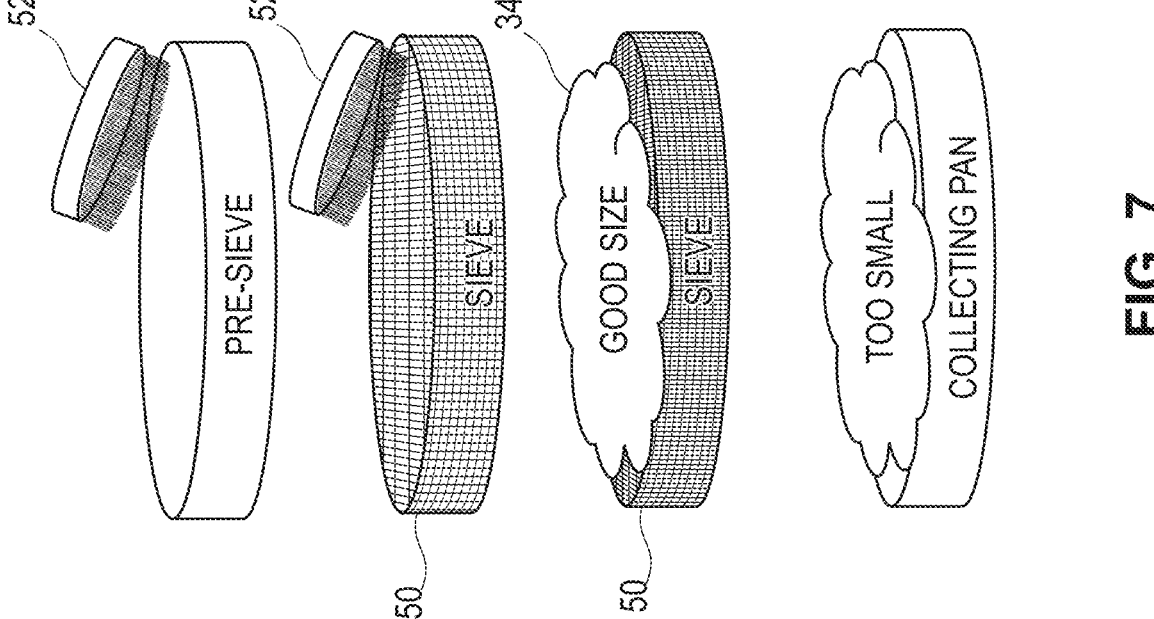
FIG. 7 illustrates the various sized sieves used to make micronized porous ceramic material that is formed after heating the mixture to remove the pore-forming agent particles from the mixture. The porous ceramic material is illustrated being micronized by passing the porous ceramic material through sieves of various sizes.

In some embodiments, the ceramic material is micronized by passing the ceramic material through a sieve 50 using a crushing force, as shown in FIGS. 7 and 8. In some embodiments, the ceramic material is micronized by a manual crusher 52, such as a pin brush and a manual sieve, shown in FIG. 7. In some embodiments, the ceramic material is micronized by an automatic crusher 54 and an automatic sieve 56, shown in FIG. 8. A plurality of sieves may be used for micronizing the ceramic material, which enables the granules to be sorted out based on size, as shown in FIG. 7. For example, a sieve with a larger mesh pore size can be used first, followed by a subsequent sieve having a smaller mesh pore size. Each sieve used in a sequence can contain smaller mesh pore sizes than the previous sieve used. In some embodiments, the mesh pore sizes of each of the sieves can be from about 0.1 mm to about 4 mm. The mesh pore sizes of each of the sieves can be from about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9 to about 4 mm.

As described above, after the micronizing step, the resulting porous ceramic granules having an average diameter from about 50 μm to 800 μm. In some embodiments, the average diameter of the granules is from about 90 μm to about 600 μm or from about 200 μm to about 500 μm. In some embodiments, the average diameter of the granules may be from about 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795 to about 800 $\mu$m.

After the micronizing step, in some embodiments, the porous ceramic granules can be optionally heated a second time to further debind the granules. This additional heat treatment can heat the porous ceramic granules at a temperature from about 200° C. to about 650° C. for a set period of time. The temperature can be from about 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645 to about 650° C. The heat treatment can be administered over a period of time, such as, from about 1 hour to about 5 hours. In some embodiments, the heat treatment is administered from about 1, 2, 3, 4 to about 5 hours.

A sintering step (58) can then be applied to the porous ceramic granules to increase the cohesion and rigidity of the granules, as shown in FIG. 1. The resulting granules are microporous with controlled interconnections and having an outer surface comprising a plurality of concave shapes, shown in FIG. 9 and as described herein.

The sintering step can occur in an oven at a temperature from about 1000° C. to about 1400° C. for a period of time. In some embodiments, the temperature is from about 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390 to about 1400° C. The sintering step can be administered for a period of time from about 1 to about 10 hours. In some embodiments, the period of time is from about 1, 2, 3, 4, 5, 6, 7, 8, 9 to about 10 hours.

Figure 10:
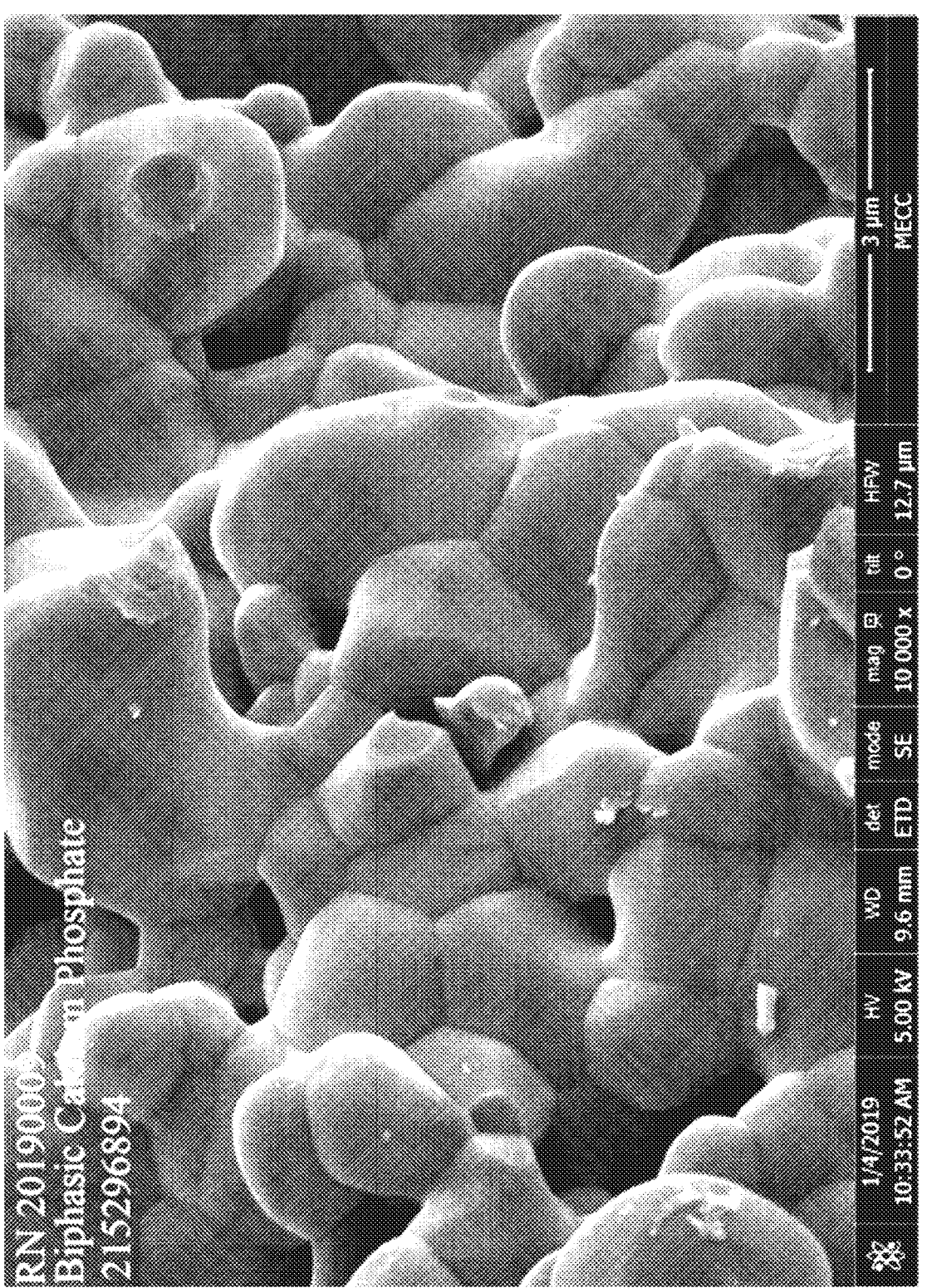
FIG. 10 is a SEM micrograph of the porous ceramic granules. As shown, the granules contain microporosity.

As described above, the porous ceramic granules each have a microporosity and the diameter of each of the micropores is from about 0.01 to about 10 microns, as shown in the SEM micrograph of FIG. 10. In some embodiments, the diameter of each of the micropores is from about 0.1 to about 10 microns or from about 1 to about 10 microns. In some embodiments, the diameter of each of the micropores can be from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9 to about 10 microns. In some embodiments, the porous ceramic granules have a percent microporosity from about 10 to about 100% or from about 10, 20, 30, 40, 50, 60, 70, 80, 90 to about 100%.

Figure 9:
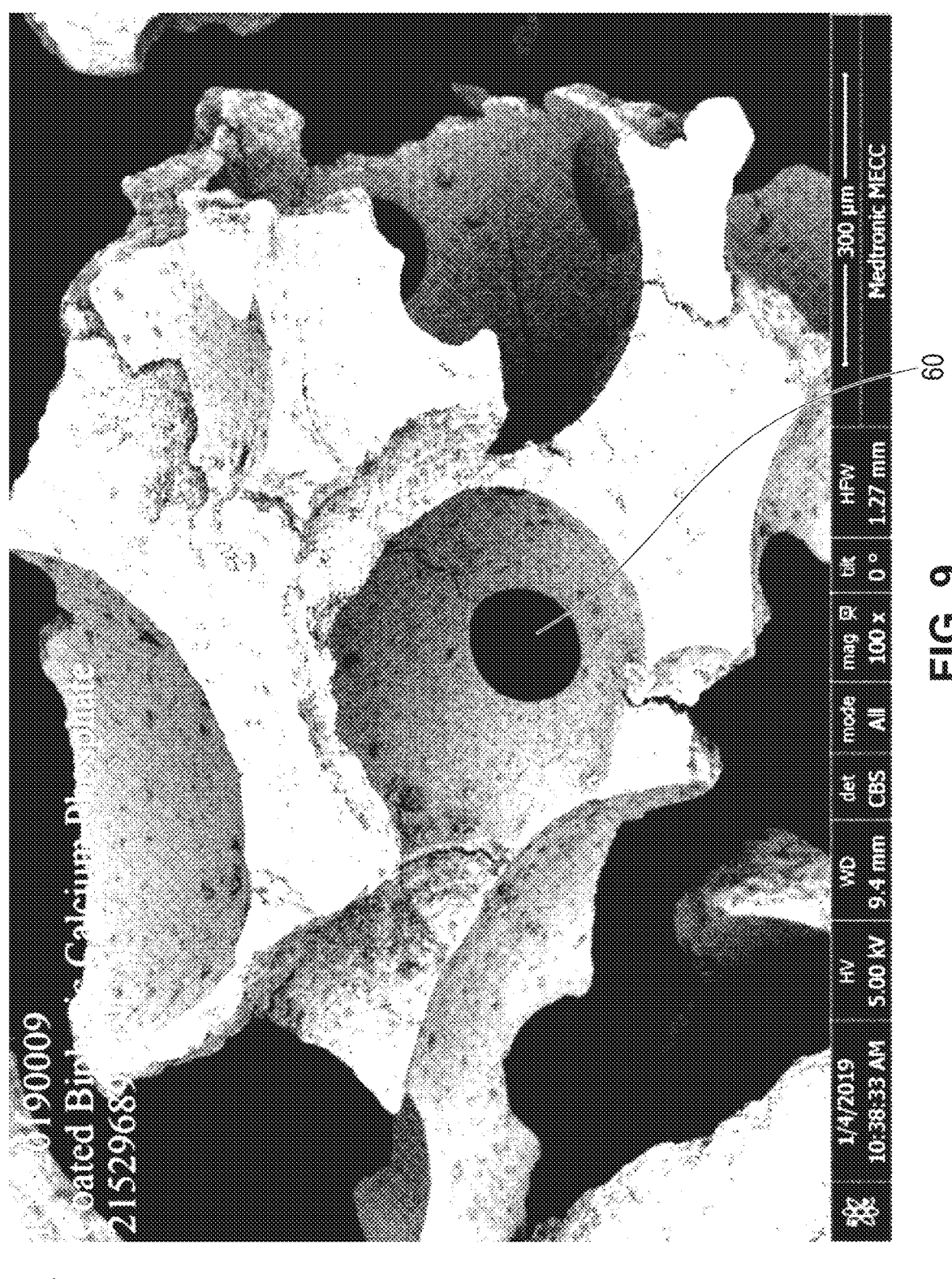
FIG. 9 is a SEM micrograph of the porous ceramic granules. The micrograph shows that the surface of the porous ceramic granules each have a concavity between 400 to about 600 microns.

The method described herein causes the porous ceramic granules to have an outer surface comprising a plurality of concave shapes 60, as shown in the SEM micrograph of FIG. 9. These concave surface features provide the granules with an irregular shape. The concave shapes can be disc like in appearance and can be a particular size. The concave shapes can each have a diameter from about 50 to about 1000 microns or from about 400 to about 600 microns. In some embodiments, each diameter can be from about 50, 75, 100, 125, 150, 175, 200, 225, 250, 275, 300, 325, 350, 375, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 625, 650, 675, 700, 725, 750, 775, 800, 825, 850, 875, 900, 925, 950, 975 to about 1000 microns. In some embodiments, the micronizing step is the step that causes the porous ceramic granules to have the concave shapes on the outer surface.

When disposed in a bone graft, the concave surfaces on the outer surface of each granule can facilitate an increase in new bone attachment since the surface makes new bone attachment easier (e.g., vascularization and penetration of associated cells) than attachment would be on a standard ceramic granule. In some embodiments, the porous ceramic granules facilitate rapid and homogeneous osseointegration which supports bone healing by acting as a scaffold over which bone can grow.

Each of the porous ceramic granules have a Brunauer-Emmett-Teller (BET) surface area from about 0.2 to about 10 m²/g. The BET surface area can be from about 0.2, 0.3, 0.4, 0.5, 0.6, 0.7, 0.8, 0.9, 1, 2, 3, 4, 5, 6, 7, 8, 9 to about 10 m²/g. The increase in surface area further facilitates new bone growth by allowing the granules to dissolve and release calcium faster than a regular granule would.

In some embodiments, the porous ceramic granules are in an amorphous form, a crystalline form or a combination thereof. When the porous ceramic granules are a combination of amorphous and crystalline, the granules can be from about 2 to about 98% amorphous to from about 98 to about 2% crystalline. When the granules are a combination of amorphous and crystalline, the granules can be from about 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96 to about 98% amorphous and from about 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96 to about 98% crystalline.

The method can also include a sterilization step (62), as shown in FIG. 1. In some embodiments, the porous ceramic granules can be sterilized by gamma radiation at a dose of about 15 kGy to about 40 kGy or about 25 kGy to about 40 kGy.

The porous ceramic granules can be packaged and stored for use. In various embodiments, the granules when packaged, can be sterilized by radiation in a terminal sterilization step. Terminal sterilization of a product provides greater assurance of sterility than from processes such as an aseptic process, which require individual product components to be sterilized separately and the final package assembled in a sterile environment.

In various embodiments, gamma radiation is used in the terminal sterilization step, which involves utilizing ionizing energy from gamma rays that penetrates deeply into the granules. Gamma rays are highly effective in killing microorganisms, they leave no residues nor have sufficient energy to impart radioactivity to the composition. Gamma rays can be employed when the granules are in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize the granules. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize the granules, including, but not limited to, gas sterilization, such as, for example, with ethylene oxide or steam sterilization.

In some embodiments, additional synthetic ceramics can be used to form the porous ceramic granules. The synthetic ceramics disclosed herein may be selected from one or more materials comprising calcium phosphate ceramics or silicon ceramics. Biological glasses such as calcium-silicate-based bioglass, silicon calcium phosphate, tricalcium phosphate (TCP), biphasic calcium phosphate, calcium sulfate, hydroxyapatite, coralline hydroxyapatite, silicon carbide, silicon nitride ($Si_3N_4$), and biocompatible ceramics may be used. In some embodiments, the ceramic is tri-calcium phosphate or biphasic calcium phosphate and silicon ceramics. In some embodiments, the ceramic is tricalcium phosphate.

In some embodiments, the ceramics are a combination of a calcium phosphate ceramic and a silicon ceramic. In some embodiments, the calcium phosphate ceramic is resorbable biphasic calcium phosphate (BCP) or resorbable tri-calcium phosphate (TCP).

In some embodiments, the biphasic calcium phosphate can have a tricalcium phosphate:hydroxyapatite weight ratio of about 50:50 to about 95:5, about 70:30 to about 95:5, about 80:20 to about 90:10, or about 85:15.

The ceramics of the disclosure may also be oxide ceramics such as alumina ($Al_2O_3$) or zirconia ($ZrO_2$) or composite combinations of oxides and non-oxides such as silicon nitride.

The porous ceramic granules can be used in a bone graft in any suitable application. For example, the granules can be administered in a bone graft which can be utilized in a wide variety of orthopedic, periodontal, neurosurgical, oral and maxillofacial surgical procedures such as the repair of simple and/or compound fractures and/or non-unions; external and/or internal fixations; joint reconstructions such as arthrodesis; general arthroplasty; cup arthroplasty of the hip; femoral and humeral head replacement; femoral head surface replacement and/or total joint replacement; repairs of the vertebral column including spinal fusion and internal fixation; tumor surgery, e.g., deficit filling; discectomy; laminectomy; excision of spinal cord tumors; anterior cervical and thoracic operations; repairs of spinal injuries; scoliosis, lordosis and kyphosis treatments; intermaxillary fixation of fractures; mentoplasty; temporomandibular joint replacement; alveolar ridge augmentation and reconstruction; inlay implantable matrices; implant placement and revision; sinus lifts; cosmetic procedures; etc. Specific bones which can be repaired herein include the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal and/or metatarsal bones.

In accordance with some embodiments, the granules may be treated or chemically modified with one or more bioactive agents or bioactive compounds. "Bioactive agent" or "bioactive compound," as used herein, refers to a compound or entity that alters, inhibits, activates, or otherwise affects biological or chemical events. For example, bioactive agents may include, but are not limited to, osteogenic or chondrogenic proteins or peptides; DBM powder; collagen, insoluble collagen derivatives, etc., and soluble solids and/or liquids dissolved therein; anti-AIDS substances; anti-cancer substances; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin, etc.; immunosuppressants; anti-viral substances such as substances effective against hepatitis; enzyme inhibitors; hormones; neurotoxins; opioids; hypnotics; anti-histamines; lubricants; tranquilizers; anti-convulsants; muscle relaxants and anti-Parkinson substances; anti-spasmodics and muscle contractants including channel blockers; miotics and anti-cholinergics; anti-glaucoma compounds; anti-parasite and/or anti-protozoal compounds; modulators of cell-extracellular matrix interactions including cell growth inhibitors and antiadhesion molecules; vasodilating agents; inhibitors of DNA, RNA, or protein synthesis; anti-hypertensives; analgesics; anti-pyretics; steroidal and non-steroidal anti-inflammatory agents; anti-angiogenic factors; angiogenic factors and polymeric carriers containing such factors; anti-secretory factors; anticoagulants and/or antithrombotic agents; local anesthetics; ophthalmics; prostaglandins; anti-depressants; anti-psychotic substances; anti-emetics; imaging agents; biocidal/biostatic sugars such as dextran, glucose, etc.; amino acids; peptides; vitamins; inorganic elements; co-factors for protein synthesis; endocrine tissue or tissue fragments; synthesizers; enzymes such as alkaline phosphatase, collagenase, peptidases, oxidases, etc.; polymer cell scaffolds with parenchymal cells; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors, or other member; tissue transplants; autogenous tissues such as blood, serum, soft tissue, bone marrow, etc.; bioadhesives; bone morphogenic proteins (BMPs); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, e.g., interleukin-1 (IL-1), interleukin-2 (IL-2); human alpha thrombin; transforming growth factor (TGF-beta); insulin-like growth factors (IGF-1, IGF-2); parathyroid hormone (PTH); platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digesters; antitumor agents; cellular attractants and attachment agents; immuno-suppressants; permeation enhancers, e.g., fatty acid esters such as laureate, myristate and stearate monoesters of polyethylene glycol, enamine derivatives, alpha-keto aldehydes, etc.; and nucleic acids.

In one embodiment, the granules can include osteoinductive agents comprising one or more members of the family of Bone Morphogenetic Proteins ("BMPs"). BMPs are a class of proteins thought to have osteoinductive or growth-promoting activities on endogenous bone tissue, or function as pro-collagen precursors. Known members of the BMP family include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-14 (GDF-5), BMP-15, BMP-16, BMP-17, BMP-18 as well as polynucleotides or polypeptides thereof, as well as mature polypeptides or polynucleotides encoding the same.

BMPs utilized as osteoinductive agents comprise one or more of BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; or BMP-18; as well as any combination of one or more of these BMPs, including full length BMPs or fragments thereof, or combinations thereof, either as polypeptides or polynucleotides encoding the polypeptide fragments of all of the recited BMPs. The isolated BMP osteoinductive agents may be administered as polynucleotides, polypeptides, full length protein or combinations thereof.

Indeed, the osteoinductive factors are the recombinant human bone morphogenetic proteins (rhBMPs) because they are available in unlimited supply and do not transmit infectious diseases. In some embodiments, the bone morphogenetic protein is a rhBMP-2, rhBMP-4, rhBMP-7, or heterodimers thereof.

Recombinant BMP-2 can also be added to the granules. However, any bone morphogenetic protein is contemplated, including bone morphogenetic proteins designated as BMP-1 through BMP-18. BMPs are available from Pfizer, a Delaware corporation and the BMPs and genes encoding them may also be prepared by one skilled in the art as described in U.S. Pat. No. 5,187,076 to Wozney et al.; U.S. Pat. No. 5,366,875 to Wozney et al.; U.S. Pat. No. 4,877,864 to Wang et al.; U.S. Pat. No. 5,108,922 to Wang et al.; U.S. Pat. No. 5,116,738 to Wang et al.; U.S. Pat. No. 5,013,649 to Wang et al.; U.S. Pat. No. 5,106,748 to Wozney et al.; and PCT Patent Nos. WO93/00432 to Wozney et al.; WO94/26893 to Celeste et al.; and WO94/26892 to Celeste et al. All osteoinductive factors are contemplated whether obtained as above or isolated from bone. Methods for isolating bone morphogenetic protein from bone are described, for example, in U.S. Pat. No. 4,294,753 to Urist and Urist et al., 81 PNAS 371, 1984.

In addition to the above, the granules may include one or more members from the TGF-β superfamily. For example, the granules may include AMH, ARTN, GDF1, GDF10, GDF11, GDF15, GDF2, GDF3, GDF3A, GDFS, GDF6, GDF7, GDF8, GDF9, GDNF, INHA, INHBA, INHBB, INHBC, INHBE, LEFTY1, LEFTY2, MSTN, NODAL, NRTN, PSPN, TGFB1, TGFB2, TGFB3, FGF, basic FGF, VEGF, insulin-like growth factor, EGF, PDGF, nerve growth factor or combinations thereof.

In certain embodiments, the bioactive agent may be a drug. In some embodiments, the bioactive agent may be a small molecule, a growth factor, cytokine, extracellular matrix molecule, or a fragment or derivative thereof, for example, a protein or peptide sequence such as RGD.

Implantable Compositions

Figure 12:
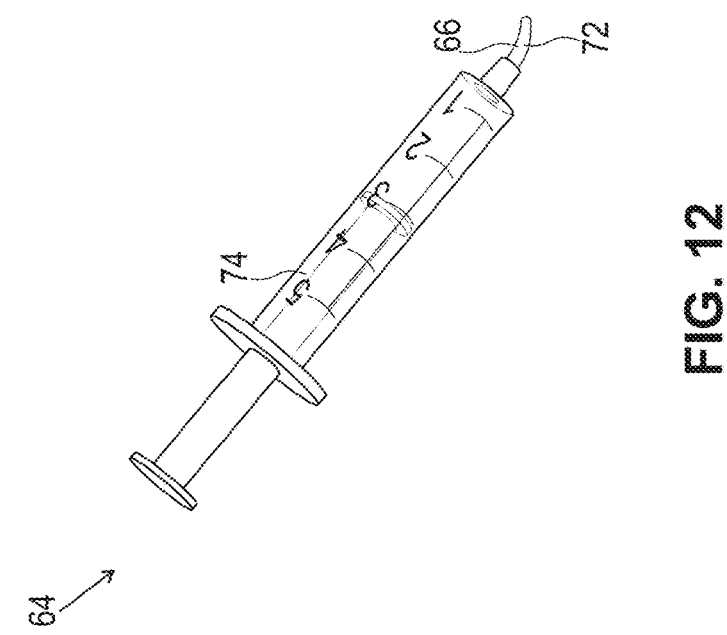
FIG. 12 is a perspective view of the composition of FIG. 11 in a non-settable flowable cohesive cement or gel form disposed within a syringe.
Figure 11:
FIG. 11 is a perspective view of an implantable composition. The implantable composition is in the form of a moldable putty. The composition comprises porous ceramic granules. The porous ceramic granules comprise hydroxyapatite in an amount of about 8 to about 22 wt. % and beta-tricalcium phosphate in an amount of about 78 to about 92 wt. % based on a total weight of a ceramic granule. The composition also includes a collagen carrier. The porous ceramic granules have an average diameter from about 50 μm to 800 μm.

As shown in FIGS. 11-16, an implantable composition 64 is provided. The implantable composition can be a bone graft such as a bone void filler and is configured to be both moldable and flowable. The composition is also ideal for bone growth and has improved handling characteristics. The composition comprises the porous ceramic granules 38, as described above with regard to the method and a collagen carrier 66, as shown in FIGS. 9 and 11, 12. The porous ceramic granules may be of a selected size, porosity, microporosity and have a specific surface area that is beneficial for bone growth when administered to a surgical site.

The porous ceramic granules comprise hydroxyapatite and beta-tricalcium phosphate. The hydroxyapatite is in an amount of about 8 to about 22 wt. % based on a total weight of a ceramic granule. The hydroxyapatite can be in a range from about 8, 9, 10, 11, 12, 13, 14, 15, 16, 17, 18, 19, 20, 21 to about 22 wt. %. In some embodiments, the hydroxyapatite can be in a range from about 1 to about 99 wt. %, such as from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 to about 99 wt. %.

The beta-tricalcium phosphate is in an amount of about 78 to about 92 wt. % based on a total weight of a ceramic granule. The beta-tricalcium phosphate can be in an amount from about 78, 79, 80, 81, 82, 83, 84, 85, 86, 87, 88, 89, 90, 91 to about 92 wt. %. In some embodiments, the beta-tricalcium phosphate can be in a range from about 1 to about 99 wt. %, such as from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 to about 99 wt. %.

The porous ceramic granules can have a calcium to phosphate ratio of between 1.0 to about 2.0. In some embodiments, the calcium to phosphate ratio is between 1.0, 1.1, 1.2, 1.3, 1.4, 1.5, 1.6, 1.7, 1.8, 1.9 to about 2.0.

The porous ceramic granules have an average diameter from about 50 μm to 800 μm. In some embodiments, the average diameter of the granules is from about 90 μm to about 600 μm or from about 200 μm to about 500 μm. In some embodiments, the average diameter of the granules may be from about 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795 to about 800 μm.

The porous ceramic granules have an interconnected porous structure having microporosity, as shown in the SEM micrograph of FIG. 10. The diameter of each of the micropores is from about 0.01 to about 10 microns. In some embodiments, the diameter of each of the micropores can be from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9 to about 10 microns.

As described above, each of the porous ceramic granules have an outer surface comprising the plurality of concave shapes 60, as shown in the SEM micrograph of FIG. 9. These concave surface features provide the granules with an irregular shape. The concave shapes can be disc like in appearance and can be a particular size. The concave shapes can each have a diameter from about 50 to about 1000 microns or from about 400 to about 600 microns. In some embodiments, each diameter can be from about 50, 75, 100, 125, 150, 175, 200, 225, 250, 275, 300, 325, 350, 375, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 625, 650, 675, 700, 725, 750, 775, 800, 825, 850, 875, 900, 925, 950, 975 to about 1000 microns.

The concave surfaces on the outer surface of each granule can facilitate an increase in new bone attachment since the surface makes new bone attachment easier (e.g., vascularization and penetration of associated cells) than attachment would be on a standard ceramic granule. In some embodiments, the porous ceramic granules facilitate rapid and homogeneous osseointegration which supports bone healing by acting as a scaffold over which bone can grow.

Each of the porous ceramic granules have a Brunauer-Emmett-Teller (BET) surface area from about 0.2 to about 10 $m^2/g$. The BET surface area can be from about 0.2, 0.3, 0.4, 0.5, 0.6, 0.7, 0.8, 0.9, 1, 2, 3, 4, 5, 6, 7, 8, 9 to about 10 $m^2/g$. The increase in surface area further facilitates new bone growth by allowing the granules to dissolve and release calcium faster than a regular granule would.

The porous ceramic granules can be in an amorphous form, a crystalline form or a combination thereof. When the porous ceramic granules are a combination of amorphous and crystalline, the granules can be from about 2 to about 98% amorphous to from about 98 to about 2% crystalline. When the granules are a combination of amorphous and crystalline, the granules can be from about 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96 to about 98% amorphous and from about 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96 to about 98% crystalline.

The porous ceramic granules can be disposed in or on the collagen carrier. The composition can include from about 50 to about 98 wt. % porous ceramic granules and from about 2 to about 50 wt. % collagen carrier based on a total weight of the composition. The composition can include from about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97 to about 98 wt. % porous ceramic granules and from about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 to about 50 wt. % collagen carrier based on the total weight of the composition.

The collagen carrier can be porcine or bovine collagen. In some embodiments, the collagen carrier comprises bovine type I collagen. The collagen carrier can be made from soluble collagen and/or insoluble collagen; and the collagen carrier can be cross-linked collagen, partially cross-linked collagen, or is not cross-linked collagen.

Figure 14:
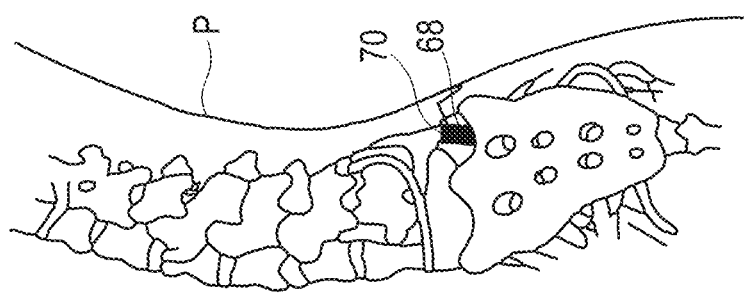
FIG. 14 is a perspective view of the putty of FIG. 13 disposed within the bone void or bone defect of the spine of a patient.
Figure 13:
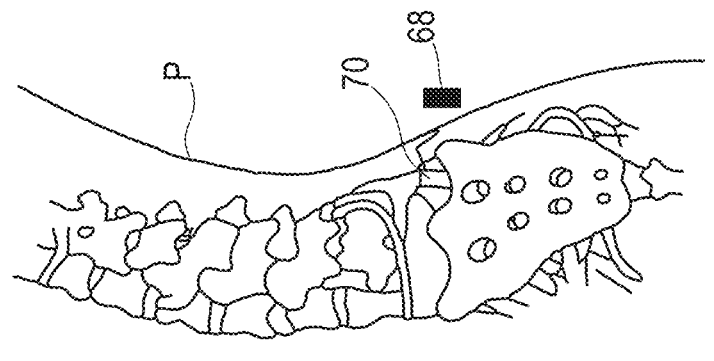
FIG. 13 is a perspective view of the composition of FIG. 11 in putty form being administered to a bone void or bone defect in the spine of a patient.
Figure 16:
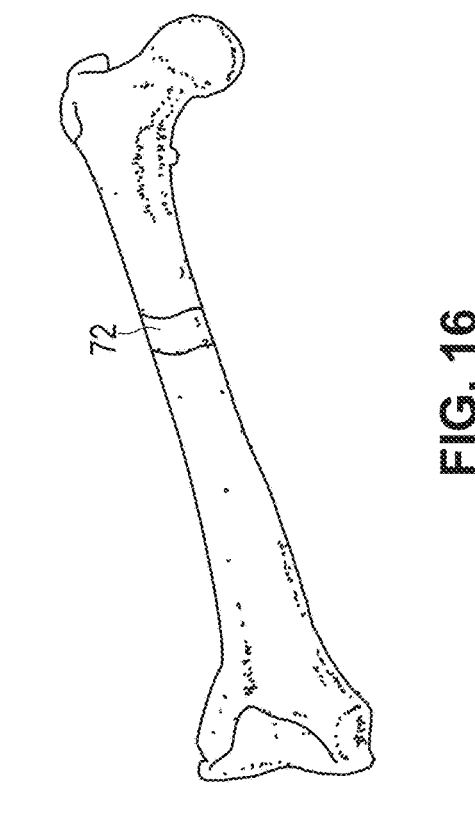
FIG. 16 is a perspective view of the non-settable flowable cohesive cement or gel form of FIG. 15 disposed within the bone void or bone defect in a patient.
Figure 15:
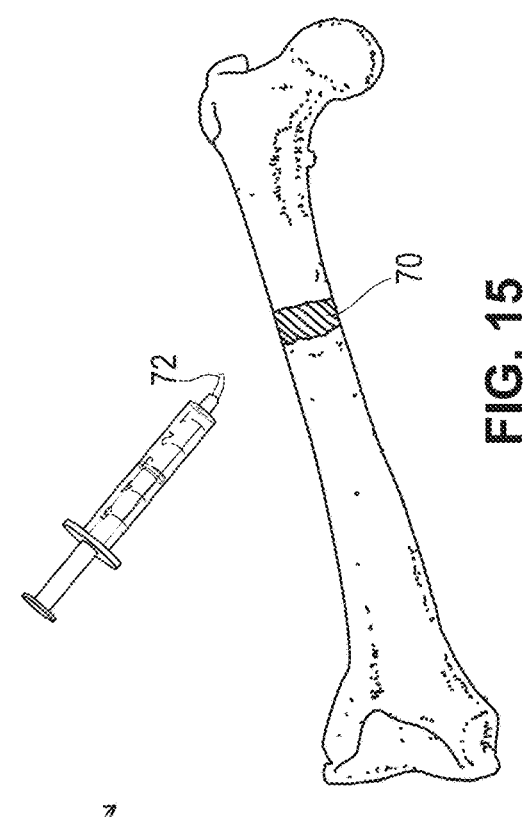
FIG. 15 is a perspective view of the non-settable flowable cohesive cement or gel form of FIG. 12 being administered to a bone void or bone defect in a patient.

The composition can be in a putty, paste, or non-settable flowable cohesive cement or gel form. The putty, paste, non-settable flowable cohesive cement or gel can be moldable and/or injectable. The composition can also be formed into a moldable putty or paste and then can be converted into a non-settable flowable cohesive cement or gel. In some embodiments, the composition can be formed into a non-settable flowable cohesive cement or gel initially and can then be converted into a putty or paste. For example, as shown in FIGS. 11 and 13-14, the composition can be administered in a putty form 68 to a surgical site such as a bone void 70 in a patient P. As shown in FIGS. 12, 15 and 16, the composition can also be administered in a non-settable flowable cohesive cement or gel form 72 to the bone void. When the composition is in the non-settable flowable cohesive cement or gel form, it is flowable and can be delivered through a syringe 74.

In some embodiments, the flowable composition has a flowable viscosity starting from about 50 Pascal-second (Pa-s), 100 Pa-s, 150 Pa-s, 200 Pa-s, 250 Pa-s, to about 300 Pa-s and reaches a higher viscosity from about 500 Pa-s, 750 Pa-s, 1000 Pa-s, 1500, 2000 Pa-s, 2500 Pa-s to about 3000 Pa-s. In some embodiments, the flowable composition has a flowable viscosity starting from about 50 Pa-s to about 3000 Pa-s and reaches a higher viscosity from about 3000 Pa-s to about 300,000 Pa-s.

The syringe, in some embodiments, used to deliver the flowable composition (e.g., the non-settable flowable cohesive cement or gel) can include a 7-8 mm bore or a 6-14 mm bore.

The composition can be lyophilized and non-hydrated for storage. A fluid such as, bone marrow aspirate, saline, sterile water for injection, phosphate buffered saline, dextrose, Ringer's lactated solution, or a combination thereof can be used to hydrate the composition prior to use. In some embodiments, when the composition is lyophilized and non-hydrated, the fluid can rehydrate the composition into the putty form. The composition can be rehydrated with a fluid to form a putty at a ratio from about 0.5 to about 1.5 vol./vol. In some embodiments, the composition can be rehydrated at a 1:1 vol./vol or a 1:1.5 vol./vol. ratio of composition to water to form the moldable paste or putty. The composition in its putty form can then be further hydrated to form a super hydrated non-settable flowable cohesive cement or gel. The putty can be further hydrated at a 150%: 200% vol./vol. ratio. Alternatively, in some embodiments, the lyophilized and non-hydrated composition can be hydrated with the fluid to form the non-settable flowable cohesive cement or gel. The composition is capable of forming into a putty and a non-settable flowable cohesive cement or gel due to the outer surface of the porous ceramic granules comprising the plurality of concave shapes, as described above and shown in the SEM micrograph of FIG. 9. The plurality of concave shapes reduces hydration time and increase hydration uniformity.

In some embodiments, prior to hydration, the composition can be sterilized by gamma radiation administered at a dose from about 15 to about 40 kGy for a period of time. The gamma radiation can be from about 15, 16, 17, 18, 19, 20, 21, 22, 23, 24, 25, 26, 27, 28, 29, 30, 31, 32, 33, 34, 35, 36, 37, 38, 39 to about 40 kGy.

The composition can have a certain density before and after hydration. For example, the composition when lyophilized and non-hydrated can have a density from about 0.2 to about 0.8 g/cc or from about 0.25 to about 0.6 g/cc. In some embodiments, the lyophilized and non-hydrated composition can have a density from about 0.2, 0.3, 0.4, 0.5, 0.6, 0.7 to about 0.8 g/cc. When the composition is hydrated, the density can be from about 1.2 to about 2.0 g/cc or from about 1.4 to about 1.6 g/cc. In some embodiments, the hydrated composition can have a density from about 1.2, 1.3, 1.4, 1.5, 1.6, 1.7, 1.8, 1.9 to about 2.0 g/cc.

The composition can have a modulus of elasticity from about 2 MPa to about 12 MPa, such as from about 2, 3, 4, 5, 6, 7, 8, 9, 10, 11 to about 12 MPa. The modulus of elasticity can change depending on the form that the composition is in (e.g., hydration level). For example, the modulus of elasticity of the composition will be higher as the hydration level is decreased and is in the putty form, and the modulus of elasticity of the composition will be lower as the hydration level is increased and is in a non-settable flowable cohesive cement or gel form. In some embodiments, the modulus of elasticity will decrease as the ceramic content is decreased.

As described above, the composition can be lyophilized to form dry, consolidated scaffolds that are formed to many shapes. Shapes include, but are not limited to indented rectangles, indented discs, indented squares, indented triangles or indented cylinders, or not indented rectangles, squares, disc, triangles, and cylinders. The indentations may be prepared to include overflow channels to be used to facilitate re-hydration with the fluid. The indentations can be similar to the indents found in U.S. Pat. No. 7,824,703, assigned to Warsaw Orthopedic, Inc., which is incorporated by reference in its entirety. In some embodiments, re-hydration can be from about 1 second to about 1 minute or from about 1 minute to about 60 minutes. In some embodiments, re-hydration can be from about 1, 5, 10, 15, 20, 25, 30, 35, 40, 45, 50, 55 seconds, 1 minute, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 to about 60 minutes.

After the composition is hydrated into putty, autograft bone can be added to the putty and the modulus of elasticity can be increased with the addition of the autograft bone. The putty will maintain its moldability and cohesiveness even with the addition of autograft bone. In some embodiments, autograft bone can also be added to the composition when it is the non-settable flowable cohesive cement or gel form.

The autograft bone can be cut into various shapes, including fibers, chips, granules, powder, shards, shavings or a combination thereof. The autograft bone can be cut into specific sizes. For example, the autograft bone can be from about 1 to about 20 mm. In some embodiments, the size of the autograft bone added to the composition can be from about 1, 2, 3, 4, 5, 6, 7, 8, 9, 10, 11, 12, 13, 14, 15, 16, 17, 18, 19 to about 20 mm.

A certain amount of autograft bone can be added to the composition, such as from about 0 to about 50 vol. % or from about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 to about 50 vol. % based on the total weight of the composition. In some embodiments, the composition can contain greater than 50 vol. % of autograft bone without the composition losing its cohesive properties.

In some embodiments, the autograft can be autograft bone chips having a size from about 1 to about 20 mm or from about 1, 2, 3, 4, 5, 6, 7, 8, 9, 10, 11, 12, 13, 14, 15, 16, 17, 18, 19 to about 20 mm.

In some embodiments, the fluid used to hydrate the composition can include sterile water, saline, phosphate buffered saline (PBS), hyaluronic acid, cellulose ethers (such as carboxymethyl cellulose), water, collagen, gelatin, autoclaved bone powder, osteoconductive carriers, whole blood, blood fractions, concentrated bone marrow aspirate, and mixtures thereof. Non-limiting examples of blood fractions include serum, plasma, platelet-rich plasma, concentrated platelet-rich plasma, platelet-poor plasma, and concentrated platelet poor plasma.

A viscosity enhancing agent can be added to the composition including, but not limited to mannitol, trehalose, hydroxypropyl cellulose, hydroxypropyl methylcellulose, hydroxyethyl methylcellulose, carboxymethylcellulose and salts thereof, Carbopol, poly-(hydroxyethyl-methacrylate), poly-(methoxyethylmethacrylate), poly(methoxyethoxyethylmethacrylate), polymethyl-methacrylate (PMMA), methylmethacrylate (MMA), gelatin, polyvinyl alcohols, propylene glycol, mPEG, PEG 200, PEG 300, PEG 400, PEG 500, PEG 600, PEG 700, PEG 800, PEG 900, PEG 1000, PEG 1450, PEG 3350, PEG 4500, PEG 8000 or combinations thereof.

In some embodiments, additional materials may be added to the composition such as one or more of poly (alpha-hydroxy acids), polyglycolide (PG), polyethylene glycol (PEG) conjugates of poly (alpha-hydroxy acids), poly-orthoesters (POE), polyaspirins, polyphosphagenes, gelatin, hydrolyzed gelatin, fractions of hydrolyzed gelatin, elastin, starch, pre-gelatinized starch, hyaluronic acid, chitosan, alginate, albumin, fibrin, vitamin E analogs, such as alpha tocopheryl acetate, d-alpha tocopheryl succinate, D,L-lactide, or L-lactide, caprolactone, dextrans, vinylpyrrolidone, polyvinyl alcohol (PVA), PVA-g-PLGA, PEGT-PBT copolymer (polyactive), methacrylates, PEO-PPO-PAA copolymers, PLGA-PEO-PLGA, PEG-PLG, PLA-PLGA, poloxamer 407, PEG-PLGA-PEG triblock copolymers, POE, SAIB (sucrose acetate isobutyrate), polydioxanone, methylmethacrylate (MMA), MMA and N-vinylpyyrolidone, polyamide, oxycellulose, copolymer of glycolic acid and trimethylene carbonate, polyesteramides, polyether ether ketone, polymethylmethacrylate, silicone, hyaluronic acid, or combinations thereof.

In some embodiments, the composition alternatively or in addition comprises at least one biodegradable polymer carrier comprising one or more of poly(lactide-co-glycolide) (PLGA), polylactide (PLA), polyglycolide (PGA), D-lactide, D,L-lactide, L-lactide, D,L-lactide-co-ε-caprolactone, L-lactide-co-ε-caprolactone, D,L-lactide-co-glycolide-co-ε-caprolactone, poly(D,L-lactide-co-caprolactone), poly(L-lactide-co-caprolactone), poly(D-lactide-co-caprolactone), poly(D,L-lactide), poly(D-lactide), poly(L-lactide), poly(esteramide), carboxymethylcellulose (CMC), alkylene oxide copolymer (AOC) or a combination thereof.

A method of making a moldable and flowable bone void filler is also provided. It is to be understood that the moldable and flowable bone void filler is the composition, as described herein. The method comprises adding porous ceramic granules to a collagen carrier, the porous ceramic granules comprising hydroxyapatite in an amount of about 8 to about 22 wt. % and beta-tricalcium phosphate in an amount of about 78 to about 92 wt. %. In some embodiments, the composition comprises from about 50 to about 98 wt. % porous ceramic granules and from about 2 to about 50 wt. % collagen carrier.

Lyophilization

As described herein, the composition can be lyophilized. The lyophilization process typically includes sublimation of water from a frozen formulation under controlled conditions. Lyophilization can be carried out using standard equipment as used for lyophilization or vacuum drying. The cycle may be varied depending upon the equipment and facilities used for the fill and finish.

Initially, in some embodiments, the composition is placed in a lyophilization chamber under a range of temperatures and then subjected to temperatures well below the freezing point of DBM, generally for several hours. After freezing is complete, the lyophilization chamber and the condenser are evacuated through vacuum pumps, the condenser surface having been previously chilled by circulating refrigerant. The condenser will have been chilled below the freezing point of the composition. Additionally, evacuation of the chamber should continue until a pressure of about 50 mTorr to about 600 mTorr, preferably about 50 to about 150 mTorr is obtained.

The lyophilized composition is then warmed under vacuum in the chamber and condenser. This usually will be carried out by warming the shelves within the lyophilizer on which the lyophilized composition rests during the lyophilization process at a pressure ranging from about 50 mTorr to about 600 mTorr. The warming process will optimally take place very gradually, over the course of several hours. Complete drying can be accomplished by stabilization of vacuum, condenser temperature and lyophilized composition shelf temperature. After the initial drying, the temperature of the lyophilized composition can be increased and maintained for several hours. Once the drying cycle is completed, the pressure in the chamber can be slowly released to atmospheric pressure (or slightly below) with sterile, dry-nitrogen gas (or equivalent gas).

In some embodiments, after lyophilization, the composition is from about 95 to about 99.5% free of moisture. The composition can be from about 95, 95.5, 96, 96.5, 97, 97.5, 98, 98.5, 99, to about 99.5% free of moisture. In some embodiments, the composition has about 0.5% to about 5% moisture content remaining after lyophilization. In various embodiments, the composition has from about 0.5, 1, 1.5, 2, 2.5, 3, 3.5, 4, 4.5 to about 5% moisture content remaining after lyophilization. The lyophilized composition is stable and can be stored at a wide range of temperatures.

These and other aspects of the present application will be further appreciated upon consideration of the following Example, which is intended to illustrate a certain particular embodiment of the application but is not intended to limit its scope, as defined by the claims.

Hydratable Putty

Figure 17:
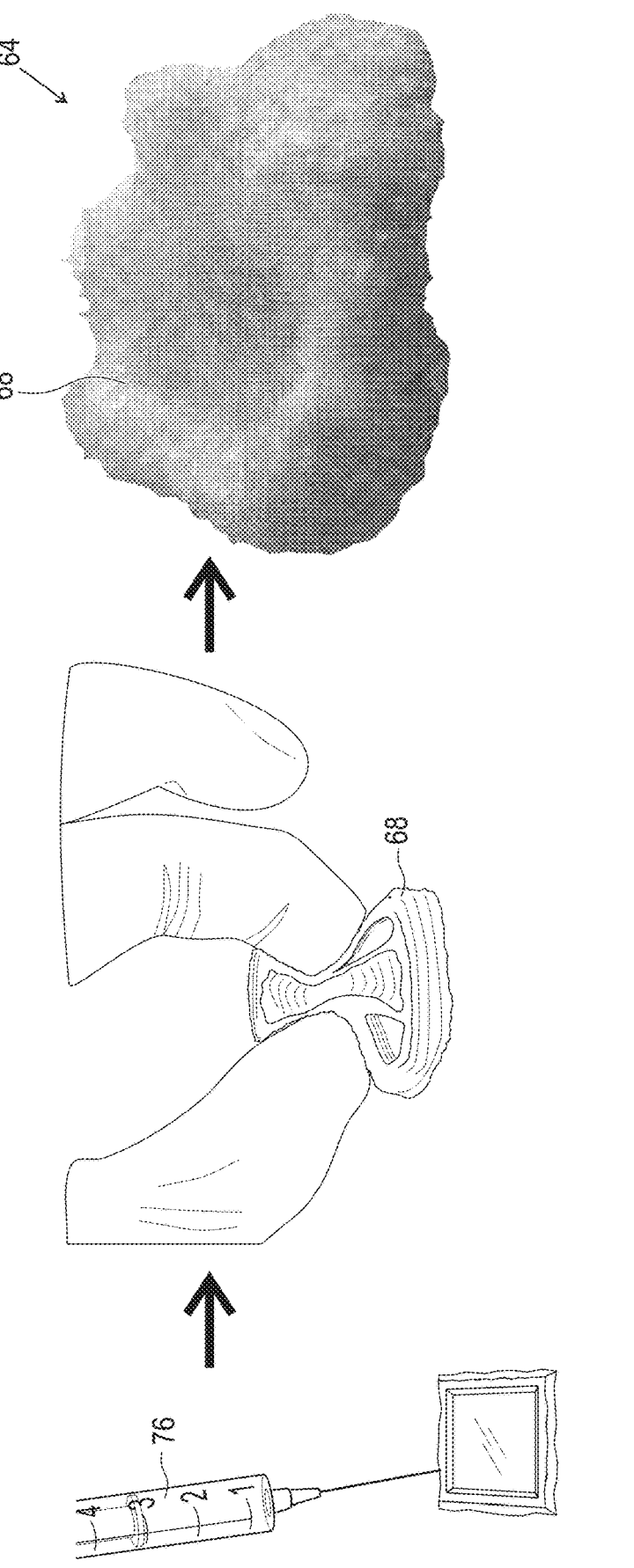
FIG. 17 is a perspective view of an implantable composition comprising a hydratable putty comprising porous ceramic granules. The porous ceramic granules have an average diameter from about 50 μm to 800 μm and comprise hydroxyapatite and beta-tricalcium phosphate. The composition also includes a collagen carrier. The implantable composition is dehydrated and then a fluid is added to the composition to form a hydrated and moldable putty.
Figure 18:
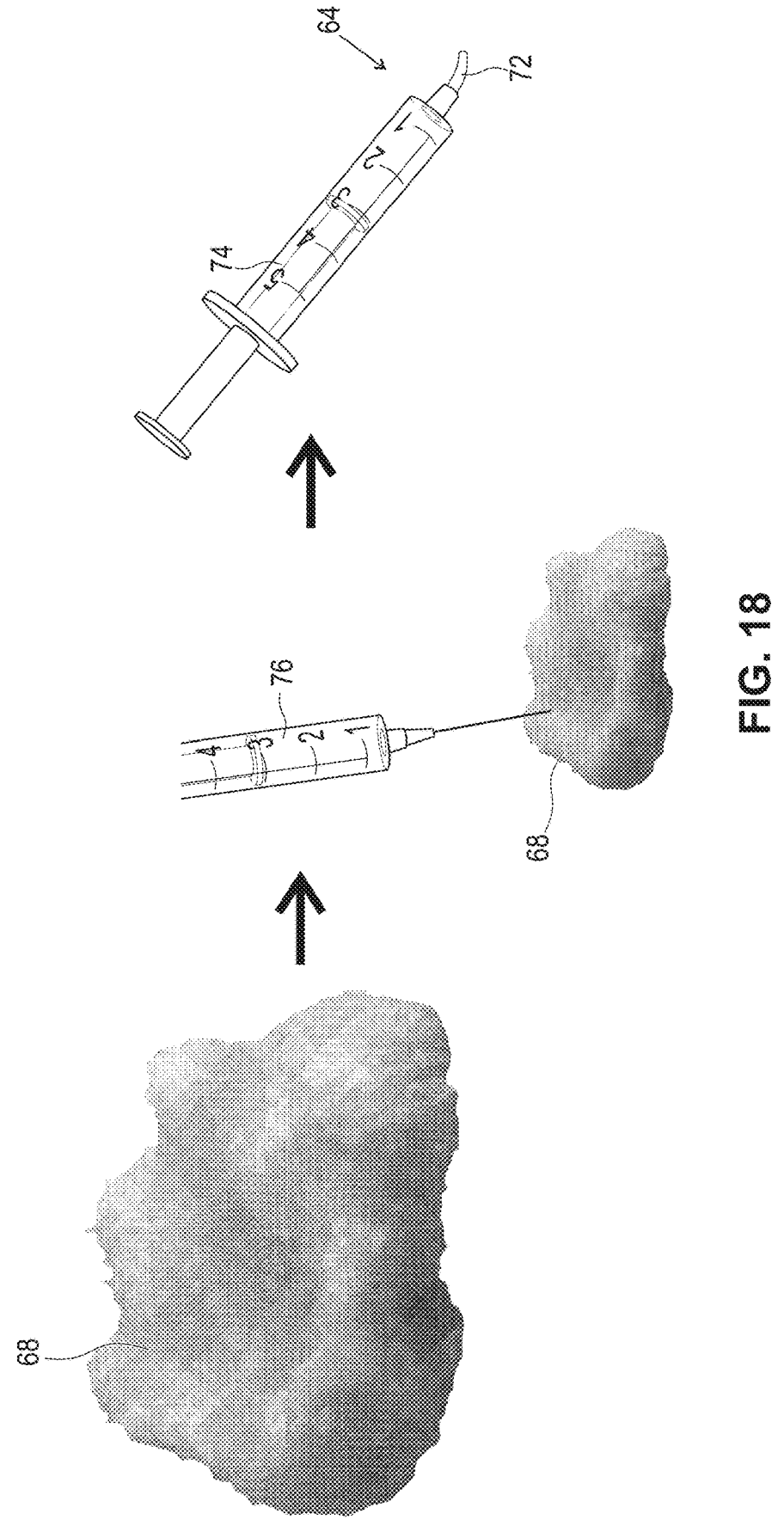
FIG. 18 is a perspective view of the implantable composition of FIG. 17 as a hydrated putty. A fluid is added a second time to the hydrated putty to form a cement. The cement can be administered through a syringe.

As shown in FIGS. 17 and 18, and described above, implantable composition 64 is provided. The implantable composition contains porous ceramic granules discussed above. The implantable composition can be in a putty or paste form such as hydratable putty 68. In some embodiments, the composition is configured to be hydrated a first time to form the putty, as shown in FIG. 17 and then hydrated a second time to form a non-settable flowable cohesive cement or gel 72, as shown in FIG. 18. In some embodiments, the composition can be initially hydrated into a non-settable flowable cohesive cement or gel. The composition is moldable, flowable and stable. The composition is configured to maintain cohesiveness and stability (e.g., will not fall apart or disintegrate during use) while in the putty, paste, cement or gel forms. The implantable composition can be converted from a putty or paste into a non-settable flowable cement or gel, and also once the composition is in the non-settable flowable cement or gel form, the composition can be readily converted into a putty or paste.

The hydratable putty includes the porous ceramic granules 38 and the collagen carrier 66, as described herein. The porous ceramic granules have an average diameter from about 50 μm to 800 μm. In some embodiments, the average diameter of the granules is from about 90 μm to about 600 μm or from about 200 μm to about 500 μm. In some embodiments, the average diameter of the granules may be from about 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795 to about 800 μm.

The porous ceramic granules are made from hydroxyapatite and beta-tricalcium phosphate. The hydroxyapatite is in an amount of about 8 to about 22 wt. % based on a total weight of a ceramic granule. The hydroxyapatite can be in a range from about 8, 9, 10, 11, 12, 13, 14, 15, 16, 17, 18, 19, 20, 21 to about 22 wt. %. In some embodiments, the hydroxyapatite can be in a range from about 1 to about 99 wt. %, as described above.

The beta-tricalcium phosphate is in an amount of about 78 to about 92 wt. % based on a total weight of a ceramic granule. The beta-tricalcium phosphate can be in an amount from about 78, 79, 80, 81, 82, 83, 84, 85, 86, 87, 88, 89, 90, 91 to about 92 wt. %. In some embodiments, the beta-tricalcium phosphate can be in a range from about 1 to about 99 wt. %, as described above.

The porous ceramic granules can have a calcium to phosphate ratio of between 1.0 to about 2.0. In some embodiments, the calcium to phosphate ratio is between 1.0, 1.1, 1.2, 1.3, 1.4, 1.5, 1.6, 1.7, 1.8, 1.9 to about 2.0.

The porous ceramic granules have an interconnected porous structure having microporosity, as described above. The diameter of each of the micropores is from about 0.01 to about 10 microns. As described above, each of the porous ceramic granules have an outer surface comprising the plurality of concave shapes 60. These concave surface features provide the granules with an irregular shape. The concave shapes can be disc like in appearance and can be a particular size. The concave shapes can each have a diameter of from about 50 to about 1000 microns or from about 400 to about 600 microns.

The porous ceramic granules have a BET surface area from about 0.2 to about 10 m²/g, and can be in an amorphous form, a crystalline form or a combination thereof. When the porous ceramic granules are a combination of amorphous and crystalline, the granules can be from about 2 to about 98% amorphous to from about 98 to about 2% crystalline.

In some embodiments, the porous ceramic granules can be disposed in or on the collagen carrier, as described herein. The composition can comprise from about 50 to about 98 wt. % porous ceramic granules and from about 2 to about 50 wt. % collagen carrier based on a total weight of the composition.

The collagen carrier can be porcine or bovine collagen. In some embodiments, the collagen carrier comprises bovine type I collagen. The collagen carrier can be made from soluble collagen and/or insoluble collagen; and the collagen carrier can be cross-linked collagen, partially cross-linked collagen, or is not cross-linked collagen. In some embodiments, the collagen can be recombinant human collagen.

The hydratable putty is configured to be hydrated with a fluid 76, as shown in FIG. 17. The fluid can include bone marrow aspirate, saline, sterile water for injection, phosphate buffered saline, dextrose, Ringer's lactated solution, or a combination thereof. In some embodiments, the fluid used to hydrate the putty can include hyaluronic acid, cellulose ethers (such as carboxymethyl cellulose), collagen, gelatin, autoclaved bone powder, osteoconductive carriers, whole blood, blood fractions, concentrated bone marrow aspirate, and mixtures thereof. Non-limiting examples of blood fractions include serum, plasma, platelet-rich plasma, concentrated platelet-rich plasma, platelet-poor plasma, and concentrated platelet poor plasma.

The ratio of fluid to hydrated putty can be from about 0.5:1 v/v to about 2:1 v/v. In some embodiments, the ratio of fluid to hydrated putty can be from about 0.5:1, 0.6:1, 0.7:1, 0.8:1, 0.9:1, 1:1, 1:1.1, 1.2:1, 1.3:1, 1.4:1, 1.5:1, 1.6:1, 1.7:1, 1.8:1, 1.9:1 to about 2:1 v/v. In some embodiments, the hydratable putty is hydrated with bone marrow aspirate at a 1:1 v/v.

The hydrated putty is formed in about 2 seconds to about 3 minutes or from about 30 seconds to about 60 seconds. In some embodiments, the hydrated putty is formed in about 2 seconds, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 seconds (1 minute), 2 minutes to about 3 minutes. In some embodiments, the dehydrated composition is rehydrated or hydrated into the putty in about 3 to about 60 minutes or from about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 to about 60 minutes.

The composition can be dehydrated before it is hydrated into the putty or the non-settable flowable cohesive cement or gel. For example, dehydration can occur by lyophilization, as described above. The density of the dehydrated composition can be between 0.2 to about 0.8 g/cc. The density of the dehydrated composition can be between 0.2, 0.3, 0.4, 0.5, 0.6, 0.7 to about 0.8 g/cc.

When the composition is in the hydratable putty form, the density of the hydratable putty can be between 1.2 to about 2.0 g/cc. The density of the hydratable putty can be between 1.2, 1.3, 1.4, 1.5, 1.6, 1.7, 1.8, 1.9 to about 2.0 g/cc.

The hydratable putty can be compression resistant and comprises a peak load of from about 30 to about 500 gram-force (gf). The peak load can be from about 30, 40, 50, 60, 70, 80, 90, 100, 120, 140, 160, 180, 200, 220, 240, 260, 280, 300, 320, 340, 360, 380, 400, 420, 440, 460, 480 to about 500 gf.

As shown in FIG. 18, to form the non-settable flowable cohesive cement or gel, the hydrated putty is hydrated a second time with an amount of fluid. The fluid can be the same or different than the fluid used to initially hydrate the putty. In some embodiments, alternatively, the non-settable flowable cohesive cement or gel can be formed from the dehydrated composition by hydrating the dehydrated composition with an amount of fluid that is greater than the amount required for the putty. The cement can be formed in about 5 to about 30 seconds or in about 5 to about 5 minutes. In some embodiments, the cement can be formed in about 5, 6, 7, 8, 9, 10, 11, 12, 13, 14, 15, 16, 17, 18, 19, 20, 21, 22, 23, 24, 25, 26, 27, 28, 29, 30 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 second, 2, 3, 4 to about 5 minutes.

The hydratable putty is configured to be hydrated with the fluid to form a non-settable flowable cohesive cement or gel and the ratio of fluid to cement or gel is about 1:1 to about 4:1 v/v. In some embodiments, the ratio of fluid to cement or gel can be from about 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, 3:1, 3.1:1, 3.2:1, 3.3:1, 3.4:1, 3.5:1, 3.6:1, 3.7:1, 3.8:1, 3.9:1 to about 4:1.

When the composition is in the non-settable flowable cohesive cement or gel form, the density of the cement or gel can be between 1.2 to about 3.0 g/cc. The density of the cement or gel can be between 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 to about 3.0 g/cc.

The cement or gel form of the composition is injectable and is less stiff than the putty form. The cement or gel maintains cohesiveness and moldability and does not exhibit granular shedding or graft disintegration. In some embodiments, before implantation, the cement or gel can dry when exposed to air, however, the cement or gel once implanted will not harden.

In some embodiments, when the composition is in the non-settable flowable cohesive cement or gel form, an amount of dehydrated composition can be added to the cement or gel to convert the cement or gel into the putty or paste form.

The composition can have a modulus of elasticity from about 2 MPa to about 12 MPa. The composition in hydrated putty or cement form can have a modulus of elasticity from about 2, 3, 4, 5, 6, 7, 8, 9, 10, 11 to about 12 MPa.

In some embodiments, the composition is rehydrated to a flowable material to form a moldable putty. In some embodiments, the moldable putty has a texture value from about 400 to about 3400. In some embodiments, the texture value of the moldable putty is from about 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300 to about 3400.

In some embodiments, the composition is lyophilized or freeze-dried. In some embodiments, the freeze-dried composition is homogeneous and does not collapse into clumps or crumble into pieces. In some embodiments, the freeze-dried composition is formed into various shapes including square shapes, rectangular shapes, circular shapes, triangular shapes, prism shapes, cylinder shapes, oval shapes, doughnut shapes, trapezoidal shapes, or disc shapes. In some embodiments, the composition is formed into a hydratable disc-shape, during freeze drying/dehydration. In some embodiments, the freeze dried composition maintains its shape after hydration prior to manipulation or molding. In some embodiments, the composition is in the form of a freeze-dried disc, which can be a round disc with indentation/reservoir in center (surrounded by sidewall as a result) for ease of fluid dispensing to hydrate. The disc mold shape can be made smaller to larger to accommodate various product sizing (such as for example, 0.75-12 ml sizes).

Figure 21:
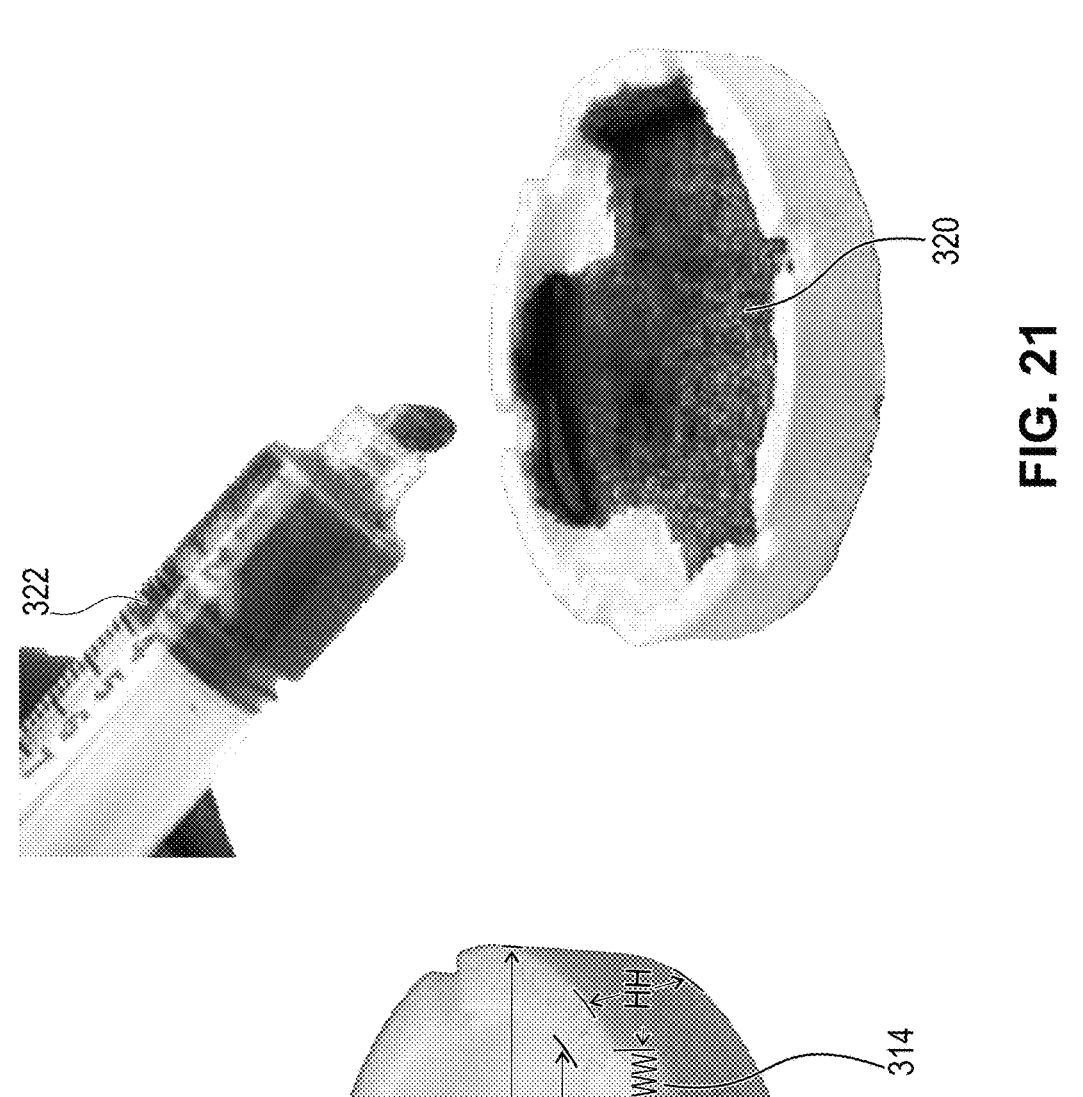
FIG. 21 is a perspective view of an implantable composition comprising a freeze-dried (e.g., lyophilized) disc. The disc has a plurality of raised portions and overflow channels, as well as a bottom and a sidewall forming an interior volume configured to hold and absorb liquid. Blood has been dispensed on a top surface of a bottom of the disc to hydrate the disc.
Figure 20:
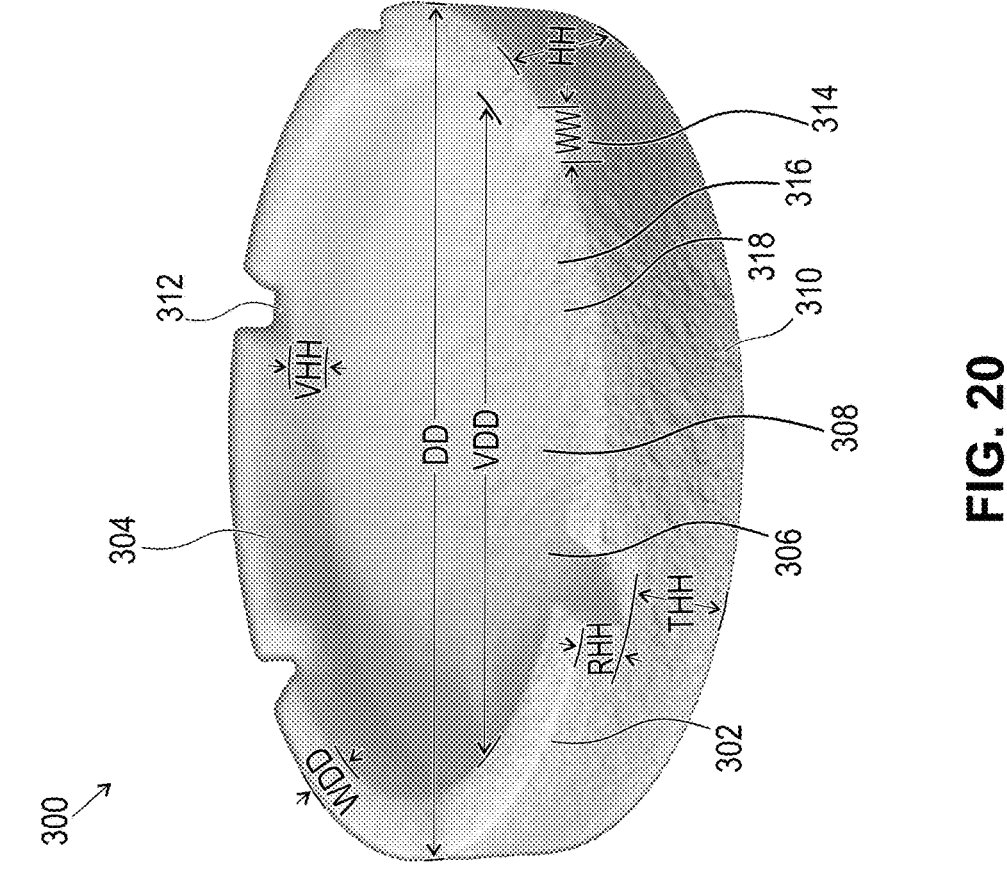
FIG. 20 is a perspective view of an implantable composition comprising a freeze-dried (e.g., lyophilized) disc that is homogeneous and does not collapse into clumps or crumble into pieces. The disc has a plurality of raised portions and overflow channels, as well as a bottom and a sidewall forming an interior volume configured to hold and absorb liquid. Therefore, the disc is hydratable.

FIG. 20 and FIG. 21 illustrate an embodiment of the freeze-dried (e.g., lyophilized) hydratable disc-shaped composition. The composition comprises disc 300. The disc has exterior surface 302 and interior surface 306. The disc has an interior surface sidewall 304 and exterior surface sidewall 310. The disc comprises region 308 to allow an internal volume of liquid and/or other material to hydrate the disc. For example, a volume of liquid 320 can be used to hydrate the disc. The interior surface comprises a fill line 312 configured to provide an indicia of a suitable amount of liquid for hydrating the composition. In some embodiments, the sidewall comprises raised portion 316 and an indent that can be an overflow channel 314. The overflow channel 314 can allow liquid to flow from the interior surface to the exterior surface to hydrate the disc. In some embodiments, a plurality of raised portions and a plurality of overflow channels of the sidewall can form a "rook" like structure with merlons and crenelles. The sidewall surrounds a circumference of the disc forming a rim 318. In some embodiments, the fill line is flush with a bottom of the overflow channel such that the excess amount of the liquid passing the fill line can pass through the overflow channel to the exterior surface of the disc. The overflow channels can allow ease and uniform hydration of the interior and exterior of the disc. Additionally, the overflow channel provides manufacturing advantages. In some embodiments, the disc is manufactured in a mold in an upside down position with the top surface of the bottom facing downward. The overflow channel is beneficial for removal of the disc from the mold. The overflow channel provides a stress point on the mold to remove the disc without damaging the interior or the rim of the disc. The disc or the circular shape of the composition contributes to a uniform hydration when the composition is hydrated. Further, the circular shape of the disc reduces the concentration stress that can occur with other shapes, such as for example, square shapes. The disc has diameter DD and height HH. The height comprises two parts including height for the bottom THH and height for the remaining raised portion RHH. The diameter ranges from about 10 mm to about 200 mm. In some embodiments, the diameter ranges from about 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, to about 200 mm. In some embodiments, the diameter ranges from about 20 mm to about 90 mm. In some embodiments, the height of the disc ranges from about 10 to about 15 mm. In some embodiments, the height of the disc ranges from about 10, 10.5, 11, 11.5, 12, 12.5, 13, 13.5, 14, 14.5 to about 15 mm. In some embodiments, the height is about 12 mm. In some embodiments, the height of the bottom ranges from about 4 to about 6 mm. In some embodiments, the height of the bottom ranges from about 4, 4.2, 4.4, 4.6, 4.8, 5, 5.2, 5.4, 5.6, 5.8 to about 6 mm. In some embodiments, the height of the bottom is about 5 mm. The diameter and the height of the bottom form an aspect ratio for the disc such that the disc can maintain its shape, texture and moldability. For example, the hydrated putty can be kneaded into a tube for injection and the injected putty can be molded into different shapes. These characteristics after the hydration can be attributed to the specific aspect ratio of the disc that allows a uniform hydration. In some embodiments, the aspect ratio of the diameter and the bottom height is from about 1:2, 1:3, 1:9, 1:10, 1:15, 1:20, 2:1, 2:8, 3:1, 3:7, 4:6, 5:5, 6:4, 7:3, 8:2, 9:1, 10:1, 15:1 to about 20:1. In some embodiments, the aspect ratio is 7:3. The disc has an interior volume VDD extending between two points of the interior surface across the center of the disc. The interior volume VDD ranges from about 5 to about 90 mm. In some embodiments, the diameter ranges from about 5, 10, 15, 20, 25, 30, 35, 40, 45, 50, 55, 60, 65, 70, 75, 80, 85, to about 90 mm. In some embodiments, the diameter ranges from about 15 mm to about 87 mm. The interior volume also has a height VHH, which extends from the top surface to the bottom edge of the overflow channel. Excess liquid, which is more than the interior volume can flow out the overflow channel. The height of the disc VHH ranges from about 4 to about 6 mm. In some embodiments, the height VHH ranges from about 4, 4.2, 4.4, 4.6, 4.8, 5, 5.2, 5.4, 5.6, 5.8 to about 6 mm. In some embodiments, the height VHH is about 5 mm. The overflow channel of the disc has a width WW from an edge of a raised portion to another edge of another adjacent raise portion. In some embodiments, the aspect ratio is calculated based on different combinations of the diameter and the height discussed herein. In some embodiments, the width of the overflow channel is from about 2.5 to about 6 mm. In some embodiments, the width is from about 2.5, 3, 3.5, 4, 4.5, 5, 5.5, to about 6 mm. In some embodiments, the width of the overflow channel is from about 3.5 mm to about 5 mm. In some embodiments, the sidewall has a thickness WDD between the exterior surface and the interior surface. The thickness of the raised portion and the overflow channel is from about 2.5 to about 6 mm. In some embodiments, the thickness is from about 2.5, 3, 3.5, 4, 4.5, 5, 5.5, to about 6 mm. In some embodiments, the thickness is from about 3.5 mm to about 5 mm. The size and the dimension of the overflow channel contribute to the amount of liquid flow from the interior of the disc. In some embodiments, a length, a width and/or a depth of the overflow channel is from about 2.5, 3, 3.5, 4, 4.5, 5, 5.5, to about 6 mm. FIG. 21 further illustrates that liquid 320 can be delivered to the interior surface of the disc by an injection device 322. In some embodiments, the liquid can be dispensed manually or through devices, such as a syringe, cannula, funnel, tube or the like. In some embodiments, the liquid can be bone marrow aspirate, blood, saline, sterile water for injection, phosphate buffered saline, dextrose, Ringer's lactated solution, or a combination thereof.

In some embodiments, the composition has a flowable viscosity starting from about 50 Pascal-second (Pa-s), 100 Pa-s, 150 Pa-s, 200 Pa-s, 250 Pa-s, to about 300 Pa-s and reaches a higher viscosity of from about 500 Pa-s, 750 Pa-s, 1000 Pa-s, 1500, 2000 Pa-s, 2500 Pa-s to about 3000 Pa-s. In some embodiments, the composition has a flowable viscosity starting from about 50 Pa-s to about 3000 Pa-s and reaches a higher viscosity from about 3000 Pa-s to about 300,000 Pa-s. In some embodiments, this allows the putty, paste, cement or gel to be moldable, and in some embodiments, injectable.

In some embodiments, autograft bone can be added to the putty, paste, cement or gel. The autograft can be easily combined with the putty, paste, cement or gel and the autograft bone can be added to the putty, paste, cement or gel in chip form. The autograft bone chips can be a selected size such as from about 1 to about 4 mm or from about 1 to about 25 mm. In some embodiments, the autograft bone chips can be from about 1, 2, 3, 4, 5, 6, 7, 8, 9, 10, 11, 12, 13, 14, 15, 16, 17, 18, 19, 20, 21, 22, 23, 24 to about 25 mm in size. The autograft bone chips can be the same or different sizes.

The autograft bone can be added to the hydrated putty in a 1:1 ratio to maintain good handling characteristics. For example, in some embodiments, 3 cc of autograft bone chips can be combined with 3 cc putty and the putty will maintain cohesiveness and moldability. Once autograft bone is incorporated into the putty, the putty can withstand additional hydration so that the handling characteristics of the putty can be modified (e.g., putty modified into a cement) and the putty will still be cohesive and moldable. In some embodiments, when autograft bone is added to the putty, the texture value, modulus of elasticity and peak load will increase compared to a putty without autograft bone. Autograft bone can be added to the putty, paste, cement or gel to modify the handling characteristics. In some embodiments, an amount of autograft bone and/or dehydrated composition can be added to the cement or gel to convert the cement or gel into the putty or paste.

In some embodiments, the cement or gel form of the composition maintains its handling characteristics when autograft bone is incorporated into the cement or gel at a 1:1 v/v ratio. In some embodiments, the autograft bone can be incorporated into the cement or gel in an amount greater than a 1:1 ratio.

The composition in the putty and/or the cement or gel form is moldable, flowable and/or injectable. The composition in the putty, paste, cement and/or gel form is cohesive where it can be manipulated, shaped and reshaped, can be pulled apart and put back together, is moldable and packable, and can be rolled and flattened.

When the composition in the cement, gel, putty or paste form is administered to a surgical site, such as a bone void, the composition will not harden upon implantation. The composition will be fixed in place where it is administered and does not migrate from the surgical site. The composition is also irrigation resistant. In some embodiments, the degradation time of the composition is from about 1 to about 2 weeks or from about 1 week to about 6 months. The composition allows hematoma formation and sufficient clotting to occur at the surgical site.

In some embodiments, when the composition does not harden upon implantation, the composition does not have a set time and may not contain a stabilizer/stabilizers (also known as stabilizing agents). In other embodiments, the composition may contain a stabilizing agent, which may be a material that will allow a calcium phosphate mineral to set when reacted after the calcium phosphate has been stored for a predetermined amount of time. In some embodiments, this time period can be one month, two months, three months, four months, five months, or six months.

Examples of the stabilizing agents that can be used in accordance with the present disclosure, include but are not limited to MgO, $MgO_2$, $Mg(OH)_2$, $MgHPO_4$, $MgHPO_4 \cdot 3H_2O$, $MgHPO_4 \cdot 7H_2O$, $Mg_3(PO_4)_2$, $Mg_3(PO_4)_2 \cdot 4H_2O$, $Mg_3(PO_4)_2 \cdot 8H_2O$, $Mg_3(PO_4)_2 \cdot 22H_2O$, $MgCO_3$, $MgCO_3 \cdot 3H_2O$, $MgCO_3 \cdot 5H_2O$, $3MgCO_3 Mg(OH)_2 3H_2O$, $MgCO_3 Mg(OH)_2 \cdot 3H_2O$, $Mg(C_3H_5O_3)_2 \cdot 3H_2O$, $MgC_2O_4 2H_2O$, $Mg(C_4H_4O_6)_2 \cdot 4H_2O$, $MgCO_3 CaCO_3$, $Mg_2P_2O_7$, $Mg(C_{12}H_{23}O_2)_{22} \cdot H_2O$, $Mg(C_{14}H_{27}O_2)_2$, $Mg(C_{18}H_{33}O_2)_2$, or $Mg(C_{18}H_{35}O_2)_2$ and/or a mixture thereof.

A method of making an implantable composition is provided. The method comprises hydrating a hydratable putty with a fluid, the hydratable putty comprising porous ceramic granules in a collagen carrier, the porous ceramic granules comprising hydroxyapatite in an amount of about 8 to about 22 wt. % and beta-tricalcium phosphate in an amount of about 78 to about 92 wt. %, the porous ceramic granules having an average diameter from about 50 μm to 800 μm.

The method further comprises hydrating the putty an additional time with a fluid to form a non-settable flowable cohesive cement or gel. The hydratable putty is moldable and can be flowable.

Figure 19:
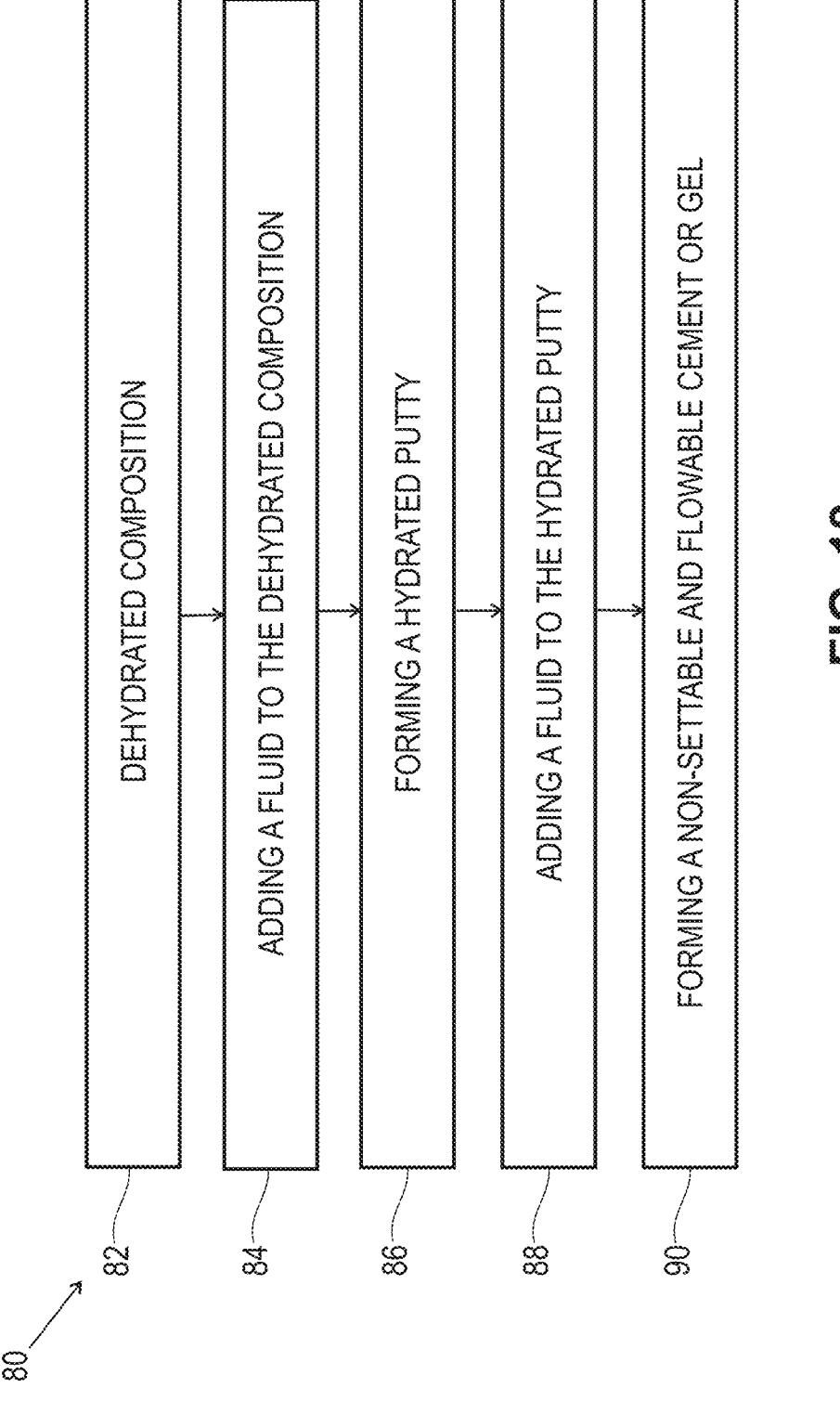
FIG. 19 is a flowchart of a method of making the implantable composition of FIG. 17. The method comprises introducing a dehydrated composition; adding a fluid to the dehydrated composition to form a hydrated putty, the hydrated putty comprising porous ceramic granules in a collagen carrier, the porous ceramic granules comprising hydroxyapatite in an amount of about 8 to about 22 wt. % and beta-tricalcium phosphate in an amount of about 78 to about 92 wt. %, the porous ceramic granules having an average diameter from about 50 μm to 800 μm; and adding a fluid to the hydrated putty to form a cement.

In some embodiments, as shown in the flowchart of FIG. 19, a method of making 80 the implantable composition is provided. The method comprises introducing the dehydrated composition 82; adding a fluid to the dehydrated composition 84 to form a hydrated putty 86, the hydrated putty comprising porous ceramic granules in a collagen carrier, the porous ceramic granules comprising hydroxyapatite in an amount of about 8 to about 22 wt. % and beta-tricalcium phosphate in an amount of about 78 to about 92 wt. %, the porous ceramic granules having an average diameter from about 50 μm to 800 μm; and adding a fluid to the hydrated putty 88 to form a non-settable flowable cohesive cement or gel 90. It is to be understood that the composition is the composition as described above.

Kits

In some embodiments, the composition and/or the porous ceramic granules alone may be packaged in a moisture resistant sterile package. In use, the porous ceramic granules can be added to a bone graft or the composition with the porous ceramic granules within or on the composition can be administered to an orthopedic site.

In various embodiments, a kit is provided comprising the composition and/or the porous ceramic granules separate from the composition. The kit may include additional parts along with the composition or granules combined together to be used to administer the bone graft (e.g., wipes, needles, syringes, mixing syringe or other mixing devices, etc.). The kit may include the porous ceramic granules or the porous ceramic granules already added to composition in a first compartment. The second compartment may include the composition if the granules have not been added to the bone graft and any other instruments needed for the delivery. A third compartment may include a fluid for hydrating the composition. A fourth compartment may include gloves, drapes, wound dressings and other procedural supplies for maintaining sterility of the implanting process, as well as an instruction booklet, which may include a chart that shows how to administer the composition. A fifth compartment may include additional needles and/or sutures. Each tool may be separately packaged in a plastic pouch that is sterilized. A sixth compartment may include an agent for radiographic imaging. A cover of the kit may include illustrations of the implanting procedure and a clear plastic cover may be placed over the compartments to maintain sterility. In some embodiments, the composition within the kit is pre-formed into a moldable putty or paste or a non-settable flowable cohesive cement or gel.

In some embodiments, the composition separate or in a kit can have a shelf life from 3 to about 5 years.

Texture Value

The handling characteristics (e.g. texture, compressive resistance, modulus of elasticity, and flowability, etc.) of the composition can be a factor for the type of implantation and use. Qualitative handling evaluation of the composition can be performed to confirm cohesive and adhesive properties useful to the compositions' moldability, modularity, the composition's ability to be combine with other bone material, and versatility. In some embodiments, the composition of the present application has a texture value from about 600 to about 3400. In some embodiments, the composition has a texture value from about 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300 to about 3400. In some embodiments, the composition has a texture value from about 1100 to about 3400. In some embodiments, the composition has a texture value from about 700 to about 2300.

The texture value can be measured with and without addition of liquid to the composition. For example, the texture value of the implantable composition can be measured when the composition is hydrated with liquid, for example, bone marrow aspirate, blood, saline, sterile water for injection, phosphate buffered saline, dextrose, Ringer's lactated solution, or a combination thereof. In some embodiments, the texture value can be measured for anhydrous, dried and/or lyophilized compositions.

The freeze dried composition's aging characteristics can be a factor in its application and use. Aging characteristics of a freeze dried composition can include the composition's ability to maintain a certain texture value upon rehydration over time. In some embodiments, the composition is able to maintain a texture value from about 600 to about 3400 for a 24 month period. In some embodiments, the composition is able to maintain the texture value for from about 1, 2, 3, 4, 5, 6, 7, 8, 9, 10, 11, 12, 13, 14, 15, 15, 17, 18, 19, 20, 21, 22, 23, 24, 25, 26, 27, 28, 29, 30, 31, 32, 33, 34, 35 to about a 36 month period.

These and other aspects of the present application will be further appreciated upon consideration of the following Example, which is intended to illustrate a certain particular embodiment of the application but is not intended to limit its scope, as defined by the claims.

Example 1

Porous Ceramic Granules

Porous ceramic granules are contemplated that are made from the method described in the flowchart of FIG. 1 and described above. The porous ceramic granules have an average diameter from about 50 μm to 800 μm, comprise a biphasic calcium phosphate comprising hydroxyapatite in an amount of about 8 to about 22 wt. % and beta-tricalcium phosphate in an amount of about 78 to about 92 wt. %, have a microporosity and the diameter of each of the micropores is from about 0.1 to about 10 microns, comprise an outer surface comprising a plurality of concave shapes each having a diameter of from about 400 to about 600 microns and each of the porous ceramic granules have a BET surface area from about 0.2 to about 10 m$^2$/g.

Example 2

Implantable Composition

An implantable composition is contemplated that can be in the form of a moldable putty or a non-settable flowable cohesive cement or gel. The implantable composition can be dehydrated and then hydrated into a moldable putty. The moldable putty can then be further hydrated into a non-settable flowable cohesive cement or gel.

It is contemplated that the implantable composition comprises porous ceramic granules comprising hydroxyapatite in an amount of about 8 to about 22 wt. % and beta-tricalcium phosphate in an amount of about 78 to about 92 wt. % based on a total weight of a ceramic granule; and a collagen carrier. The porous ceramic granules have an average diameter from about 50 μm to 800 μm. The composition comprises from about 50 to about 98 wt. % porous ceramic granules and from about 2 to about 50 wt. % collagen carrier based on a total weight of the composition. The collagen carrier is porcine or bovine collagen and the implantable composition has a modulus of elasticity from about 2 MPa to about 12 MPa. The implantable composition can be hydrated with bone marrow aspirate.

Example 3

Implantable Composition

An implantable composition is contemplated that can be in the form of a moldable putty or a non-settable flowable cohesive cement or gel. The implantable composition can be dehydrated and then hydrated into a moldable putty and/or a non-settable flowable cohesive cement or gel.

The implantable composition comprises porous ceramic granules comprising hydroxyapatite in an amount of about 15 wt. % and beta-tricalcium phosphate in an amount of about 85 wt. % based on a total weight of a ceramic granule and a collagen carrier. The calcium to phosphate ratio is 1.525. The porous ceramic granules have an average diameter from about 200 μm to 500 μm. The composition comprises from about 77 to about 93 wt. % porous ceramic granules and from about 7 to about 23 wt. % collagen carrier based on a total weight of the composition. The collagen carrier is bovine type I collagen and the plurality of concave shapes on the outer surface of the granules each have a diameter from about 400 to about 600 microns. The porous ceramic granules contain microporosity and the volume of the microporosity is from about 0.01 to about 10 microns. Each of the porous ceramic granules have a BET surface area from about 0.2 to about 0.6 m$^2$/g. The implantable composition can be hydrated with bone marrow aspirate.

Example 4

Flowable and Moldable Composition

Background: The handling characteristics (e.g. texture, compressive resistance, modulus of elasticity, and flowability) of the composition are important for implantation and use. Qualitative handling evaluation of the composition was performed to confirm cohesive and adhesive properties critical to putty moldability, modularity, combination with autograft, and versatility in known use conditions. Quantitative testing to characterize the handling properties was also performed and the results of this testing are briefly summarized below.

Texture Value

The texture value in arbitrary units is the positive area under the curve of an unconstrained load versus displacement curve under compression. Testing was performed on 1.5 cc of material hydrated with water at various hydration ratios (0.5-1.5 vol./vol.) and formed into a 10.25 mm diameter cylinder with 18 mm height. The test articles were compressed with a 5 mm diameter piston at a crosshead speed of 1.0 mm/s for 12 s.

Texture values of ≥200 were measured for test articles measured under the above conditions. Results showed that the texture value increased as the hydration level decreased. The texture value increased as the ceramic content and the ceramic granule size was increased. An optimal texture value for the composition in the moldable putty form (hydrated at 1:1 vol./vol.) was identified to be ≥1000. A lower texture value (e.g., 200-1000) was identified to be optimal for the flowable/injectable form (hydrated at ≥1:1 vol./vol.). The composition was determined to have these texture values after gamma irradiation at 25-40 kGy.

Young's Modulus of Elasticity:

The modulus of elasticity of the composition was calculated from an unconstrained stress curve versus a strain curve when the composition was hydrated with water at various hydration ratios (0.5-1.5 vol./vol.), formed into a 10.25 mm diameter cylinder with 18 mm height, and compressed at a crosshead speed of 1.0 mm/s for 12 s.

The modulus of elasticity was calculated to be ≥2 MPa for test articles measured under the above conditions. The modulus of elasticity increased as the hydration level was decreased. The modulus of elasticity was increased as the ceramic content and ceramic granule size was increased. Optimal modulus of elasticity for the moldable putty and the flowable cement forms of the composition were identified after gamma irradiation at 25-40 kGy to be: ≥2 MPa, ≥6 MPa and ≥10 MPa.

Compressive Resistance-Peak Load

The peak load of the composition was measured from an unconstrained load versus displacement curve when the composition was hydrated with water at various hydration ratios (0.5-1.5 vol./vol.), formed into a 10.25 mm diameter cylinder with 18 mm height, and compressed at a crosshead speed of 1.0 mm/s for 12 s.

The peak load was measured to be 30≥gf≥500 for test articles measured under the above conditions. The peak load increased as the hydration level was decreased. The peak load was increased as the ceramic content and ceramic granule size was increased. Optimal peak loads for the moldable putty and flowable cement forms of the composition were identified after gamma irradiation at 25-40 kGy to be between: $30 \geq gf \geq 500$, $50 \geq gf \geq 400$ and $100 \geq gf \geq 400$.

Example 5

12-Month Aging Study

A 12-month aging study of the freeze dried composition was conducted and the texture value of water-rehydrated composition following the 12 month aging was evaluated. The results of this study are briefly summarized below.

Texture Value

The texture value in arbitrary units is the positive area under the curve of an unconstrained load versus displacement curve under compression. Samples were hydrated with water at a 1:1 ratio by mass and testing was performed on 1.5 cc of material which was formed into a 10.25 mm diameter cylinder with 18 mm height. The test articles were compressed with a 5 mm diameter piston at a crosshead speed of 1.0 mm/s for 12 s.

Three samples were tested. Each sample having 3 replicates from 3 different batches of the composition and their corresponding texture value after 12 months were tested. The results are shown in Table 5-1.

TABLE 5-1

| Batch | Sample | Sample 2 | Sample 3 |
|---|---|---|---|
| R2425 | 1143.545 | 1136.953 | 2166.097 |
| | 1687.779 | 1525.43 | 2951.51 |
| | 1106.354 | 2432.95 | 3344.412 |
| Average | 1312.56 | 1698.444 | 2820.673 |
| Standard Deviation | 325.481 | 665.096 | 599.954 |
| Coefficient of Variation | 24.797 | 39.159 | 21.27 |
| R2426 | 2521.571 | 2965.374 | 1678.804 |
| | 2574.991 | 3375.85 | 2243.523 |
| | 2903.982 | 2194.62 | 1791.78 |
| Average | 2666.848 | 2845.281 | 1904.703 |
| Standard Deviation | 207.094 | 599.702 | 298.815 |
| Coefficient of Variation | 7.765 | 21.077 | 15.688 |
| R2427 | 1431.869 | 1212.814 | 1021.685 |
| | 1378.335 | 1845.239 | 1648.128 |
| | 1664.19 | 1478.811 | 1583.909 |
| Average | 1491.465 | 1512.288 | 1417.908 |
| Standard Deviation | 151.96 | 317.539 | 344.638 |
| Coefficient of Variation | 10.189 | 20.997 | 24.306 |

Each part was tested three times yielding an average number shown in Table 5-1. The lowest texture value obtained among all the testing is 1021.685 and the highest texture value obtained among all the testing is 3375.85.

Example 6

24-Month Accelerated Aging Study

A 24-month aging study of the freeze dried composition was conducted and the texture value of water-rehydrated composition following the 24 months accelerated aging was evaluated. Accelerated aging via elevated temperatures and humidity conditions was used to simulate 24 months of real time aging. The results of this study are briefly summarized below.

Texture Value

The texture value in arbitrary units is the positive area under the curve of an unconstrained load versus displacement curve under compression. Samples were hydrated with water at a 1:1 ratio by mass and testing was performed on 1.5 cc of material which was formed into a 10.25 mm diameter cylinder with 18 mm height. The test articles were compressed with a 5 mm diameter piston at a crosshead speed of 1.0 mm/s for 12 s.

Three samples were tested. Each sample having 3 replicates from 3 different batches of the composition and their corresponding texture value after 24 months were tested. The results are shown in Table 6-1.

TABLE 6-1

| Batch | Sample 1 | Sample 2 | Sample 3 |
|---|---|---|---|
| R2425 | 1740.364 | 1501.816 | 1904.479 |
| | 1130.302 | 1268.937 | 1380.825 |
| | 2248.18 | 1586.019 | 974.354 |
| Average | 1706.282 | 1452.257 | 1419.886 |
| Standard Deviation | 559.718 | 164.248 | 466.291 |
| Coefficient of Variation | 32.803 | 11.31 | 32.84 |
| R2426 | 1201.05 | 1277.409 | 1309.887 |
| | 2065.574 | 1753.224 | 1141.593 |
| | 1683.849 | 1447.794 | 789.855 |
| Average | 1650.157 | 1492.809 | 1080.445 |
| Standard Deviation | 433.246 | 241.08 | 265.354 |
| Coefficient of Variation | 26.255 | 16.149 | 24.56 |
| R2427 | 1016.011 | 774.336 | 1106.586 |
| | 1031.101 | 904.069 | 889.664 |
| | 1172.169 | 1017.635 | 1129.346 |
| Average | 1073.093 | 898.68 | 1041.866 |
| Standard Deviation | 86.133 | 121.739 | 132.301 |
| Coefficient of Variation | 8.027 | 13.546 | 12.698 |

Each part was tested three times yielding an average number shown in Table 6-1. The lowest texture value obtained among all the testing is 774.336 and the highest texture value obtained among all the testing is 2248.18.

Although the invention has been described with reference to preferred embodiments, persons skilled in the art will recognize that changes may be made in form and detail without departing from the spirit and scope of the invention.

What is claimed is:

1. An implantable composition comprising porous ceramic granules, the porous ceramic granules having an average diameter from about 50 μm to 800 μm and comprising hydroxyapatite and beta-tricalcium phosphate; and a collagen carrier, the composition having a texture value greater than 1000, wherein the composition is in the form of a disc having a sidewall having at least one overflow channel, and wherein the disc has an interior surface and an exterior surface and the at least one overflow channel is configured to allow liquid to flow from the interior surface to the exterior surface of the disc.

2. The composition of claim 1, wherein the texture value is greater than 3000.

3. The composition of claim 1, wherein the texture value is greater than 1000 after 12 months.

4. The composition of claim 1, wherein the texture value is greater than 1000 after 24 months.

5. The composition of claim 1, wherein the composition is in a dehydrated or lyophilized form that can be hydrated with a liquid to a hydrate form.

6. The composition of claim 5, wherein the density of the dehydrated form is between 0.2 to about 0.8 g/cc and the density of the hydrated form is 1.2 to about 2.0 g/cc.

7. The composition of claim 5, wherein the hydrated form is compression resistant and comprises a peak load of from about 30 to about 500 gf.

8. The composition of claim 1, wherein the disc has an aspect ratio from about 1:2, 1:3, 1:9, 1:10, 1:15, 1:20, 2:1, 2:8, 3:1, 3:7, 4:6, 5:5, 6:4, 7:3, 8:2, 9:1, 10:1, 15:1 to about 20:1.

9. The composition of claim 1, wherein the disc comprises a fill line configured to indicate a volume of liquid to be added to the disc.

10. The composition of claim 1, wherein the composition comprises from about 50 to about 98 wt. % porous ceramic granules and from about 2 to about 50 wt. % collagen carrier based on a total weight of the composition.

11. A composition comprising porous ceramic granules, the porous ceramic granules having an average diameter from about 50 μm to 800 μm and comprising hydroxyapatite and beta-tricalcium phosphate; and a collagen carrier comprising bovine type I collagen, wherein the porous ceramic granules have a microporosity, and the diameter of each of the micropores is from about 0.01 to about 10 microns, and each of the porous ceramic granules has a Brunauer-Emmett-Teller (BET) surface area from about 0.2 to about 10 m²/g, wherein the composition comprises from about 77 to about 93 wt. % porous ceramic granules and from about 7 to about 23 wt. % of the collagen carrier, wherein the composition has a texture value greater than 1000, wherein the composition is in the form of a disc having a sidewall having at least one overflow channel, and wherein the disc has an interior surface and an exterior surface and the at least one overflow channel is configured to allow liquid to flow from the interior surface to the exterior surface of the disc.

12. The composition of claim 11, wherein (i) the composition is hydrated with a fluid to form a moldable hydrated putty where the ratio of fluid to hydrated putty is about 0.5:1 v/v to about 2:1 v/v; or (ii) the composition is hydrated with a fluid to form a non-settable flowable cohesive cement or gel and the ratio of fluid to cement or gel is about 1:1 to about 4:1 v/v.

13. The composition of claim 12, wherein the hydratable putty is hydrated with a fluid comprising bone marrow aspirate.

14. A method of making the implantable composition of claim 1, the method comprising providing the composition of claim 1 and hydrating the composition of claim 1 with a fluid to form a hydrated composition.

15. The method of claim 14, wherein (i) the composition is moldable and (ii) the composition is a non-settable flowable cohesive cement or gel.

* * * * *